(12) United States Patent
Huang et al.

(10) Patent No.: US 8,765,775 B2
(45) Date of Patent: Jul. 1, 2014

(54) ANTI-ANGIOGENIC COMPOUNDS

(75) Inventors: Danzhi Huang, Zurich (CH); Peter Kolb, Salzburg (AT); Karine Lafleur, Zurich (CH); Cristina Nevado, Zurich (CH); Amedeo Caflisch, Zurich (CH)

(73) Assignee: Universitaet Zuerich, Zurich (CH)

( * ) Notice: Subject to any disclaimer, the term of this patent is extended or adjusted under 35 U.S.C. 154(b) by 922 days.

(21) Appl. No.: 12/863,724

(22) PCT Filed: Jan. 23, 2009

(86) PCT No.: PCT/EP2009/000439
§ 371 (c)(1),
(2), (4) Date: Oct. 12, 2010

(87) PCT Pub. No.: WO2009/092602
PCT Pub. Date: Jul. 30, 2009

(65) Prior Publication Data
US 2011/0077401 A1    Mar. 31, 2011

(30) Foreign Application Priority Data
Jan. 24, 2008   (EP) .................................... 08001289

(51) Int. Cl.
*A61K 31/522*   (2006.01)
*C07D 473/04*   (2006.01)
*C07D 473/06*   (2006.01)

(52) U.S. Cl.
CPC ............ *C07D 473/06* (2013.01); *C07D 473/04* (2013.01); *A61K 31/522* (2013.01)
USPC .......................................... 514/267; 544/251

(58) Field of Classification Search
CPC ... A61K 31/522; C07D 473/04; C07D 473/06
USPC .......................................... 514/267; 544/251
See application file for complete search history.

(56) References Cited

FOREIGN PATENT DOCUMENTS

WO    2006/083916 A2    8/2006

OTHER PUBLICATIONS

Priimenko, et al., Synthesis and Pharmacological Activity of 6,8-dimethylimidazo[1,2-f]xanthines, Khimiko-Farmatsevticheskii Zhurnal, 18(12), 1456-61 (1984).*
Garmash, S. N. et al: "Synthesis and biological activity of 3-formyl-8-methyl-6H-imidazo[1,2-f]xanthin e derivatives" in Khimiko-Farmatsevticheskii Zhurnal, vol. 18, No. 3, 1984, pp. 307-311, XP002524016.
Priimenko, B. A. et al: "Heterocyclic derivatives of purines. 3. Synthesis and mass-spectrometric study of imidazo [I,2-f] purine" in Khimiya Geterotsiklicheskikh Soedinenii, vol. 8, 1980, pp. 1125-1129, XP002524017.
Lafleur et al, "Structure-Based Optimization of Patent and Selective Inhibitors of the Tyrosine Kinase Erythropoietin Producing Human Hepatocellural Carcinoma Receptor B4 (EphB4)," J. Med. Chem. vol. 52, 2009, pp. 6433-6446.

* cited by examiner

*Primary Examiner* — Erich A Leeser
(74) *Attorney, Agent, or Firm* — Joyce von Natzmer; Agris & von Natzmer LLP

(57) ABSTRACT

The invention relates to compounds of formula 1, tautomers and salts thereof, wherein $R^1$, $R^2$, $R^3$, $R^4$, and $R^5$ have the meanings indicated in the specification. These compounds are receptor tyrosine kinase EphB4 inhibitors useful for the treatment of angiogenesis dependent cancers and intraocular neovascular syndromes. The invention further relates to a method termed ALTA (anchor-based library tailoring) of selecting compounds from a large compound library for screening as EphB4 inhibitors by computational procedures.

8 Claims, 3 Drawing Sheets

ANTI-ANGIOGENIC COMPOUNDS

This is the U.S. national stage of International application PCT/EP2009/000439, filed Jan. 23, 2009 designating the United States and claiming priority to European application EP 08001289.1, filed on Jan. 24, 2008, which are incorporated herein by reference in their entirety.

FIELD OF THE INVENTION

The invention relates to compounds and pharmaceutical preparations useful in the treatment of angiogenesis dependent cancers and intraocular neovascular syndromes, and a computational method for selecting compounds for screening.

BACKGROUND OF THE INVENTION

The receptor tyrosine kinase EphB4 is a highly attractive angiogenic target involved in many types of cancer (Cheng N., Brantley D. M. and Chen J., Cytokine Growth Factor Rev 2002, 13:75-85). Angiogenesis, the formation of new blood vessels from pre-existing vasculature, is a multi-step process involving many various factors, which stimulate endothelial cell proliferation, migration, and assembly, as well as recruitment of perivascular cells and extracellular matrix remodelling. Angiogenesis is implicated in the pathogenesis of a variety of disorders, including solid tumours, intraocular neovascular syndromes such as proliferative retinopathies or age-related macular degeneration (AMD), rheumatoid arthritis, and psoriasis.

Ephrins and their receptors were first identified in studies for neuronal growth during development. Unlike other families of receptor tyrosine kinases, which bind soluble ligands, ephrin receptors interact with cell surface-bound ephrin ligands. Ephrins attach to the cell membrane either through a glycosylphosphatidyl inositol anchor (ephrin A) or a transmembrane domain (ephrin B). Ephrin receptors are likewise divided in two subclasses EphA and EphB, depending on the type of interaction with their ligands ephrin A or B. Ephrins and their receptors have been shown to play an essential role in vascular development during embryogenesis and in adult angiogenesis, as key regulators of vascular assembly, arterio-venous differentiation, and boundary formation. Both EphA and EphB receptors and their ligands are involved in vascular development. Especially, ephrin B2 is expressed in arterial endothelial cells, whereas its cognate receptor, EphB4 is expressed in venous endothelial cells. EphB4 (also named HTK) and its ligand, ephrin B2 (HTKL), play important roles in establishing and determining vascular networks. Blocking this receptor/ligand pair inhibits the end stage of tumour blood vessel formation, as well as causes direct growth inhibition of certain cancers.

EphB4 seems to be rather recalcitrant to inhibition because, despite its potential therapeutic importance, only two series of non-peptidic small molecule inhibitors have been reported in the literature up to date (Miyazaki Y. et al., Bioorg Med Chem Lett 2007, 17:250-254). Examples of angiogenesis inhibitors are found in WO 2006/131003 and WO 2007/062805.

Docking is an important and successful method in computer-aided drug design. However, there is a large and increasing discrepancy between the number of small molecules available in computer-readable format (in the order of $10^7$-$10^8$ compounds, not counting those generated by de novo design programs) and the amount of molecules that can be efficiently processed by high-throughput approaches in silico or in vitro (in the order of $10^5$-$10^6$). Moreover, it is highly inefficient to use computational resources or robotic systems and chemical reagents for compounds that have a low chance of binding to the target protein. The essential question is how to utilize (structural) information of the target to pre-select the molecules that are most likely to show binding and inhibitory activity.

Several in silico fragment-based approaches, e.g., SEED, MCSS and FFLD, and in vitro "needle screening" procedures have been suggested in the prior art. Needle- or anchor-based in vitro screening has been applied to a wide range of enzymes including thrombin, DNA gyrase, and protein tyrosine kinases. In addition, others have tried to reduce docking computation times by selecting ligands through the application of pharmacophore constraints and were able to identify inhibitors of enzymes.

SUMMARY OF THE INVENTION

The invention relates to compounds of the formula 1

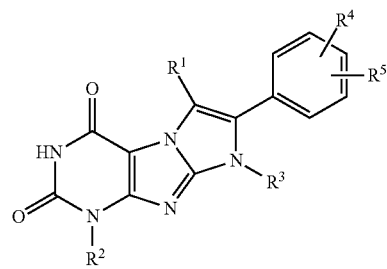

wherein
$R^1$ is alkyl, cycloalkyl, heterocyclyl, aryl-lower alkyl, cycloalkyl-lower alkyl, heteroaryl-lower alkyl, hydroxy-lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, aryl, heteroaryl, hydroxy, lower alkoxy, halo-lower alkoxy, lower alkoxy-lower alkoxy, aryloxy, hetero-aryloxy, formyloxy, lower alkylcarbonyloxy, arylcarbonyloxy, heteroarylcarbonyloxy, sulfhydryl, alkylthio, arylthio, heterarylthio, alkylsulfinyl, arylsulfinyl, heteroarylsulfinyl, alkylsulfonyl, arylsulfonyl, heteroarylsulfonyl, aminosulfonyl, lower alkylaminosulfonyl, amino, unsubstituted or substituted by one or two substitutents selected from lower alkyl, cycloalkyl, aryl-lower alkyl, cycloalkyl-lower alkyl, heteroaryl-lower alkyl, hydroxy-lower alkyl, lower alkoxy-lower alkyl, or substituted by one substituent aryl or heteroaryl and optionally another substituent lower alkyl, or substituted by one substituent formyl, lower alkylcarbonyl, arylcarbonyl, heteroarylcarbonyl, lower alkoxycarbonyl or lower alkoxy-lower alkoxycarbonyl, or wherein the two substituents on nitrogen form together with the nitrogen heterocyclyl;

formyl, lower alkylcarbonyl, arylcarbonyl, heteroarylcarbonyl, carboxy, lower alkoxycarbonyl, lower alkoxy-lower alkoxycarbonyl;

aminocarbonyl and aminothiocarbonyl wherein amino is unsubstituted or substituted by one or two substitutents selected from lower alkyl, cycloalkyl, aryl-lower alkyl, cycloalkyl-lower alkyl, heteroaryl-lower alkyl, hydroxy-lower alkyl, lower alkoxy-lower alkyl, or substituted by one substituent aryl or heteroaryl and optionally another substituent lower alkyl, or wherein the two substituents on nitrogen form together with the nitrogen heterocyclyl;
cyano, halogen, or nitro;
$R^2$ is hydrogen, lower alkyl, aryl-lower alkyl, cycloalkyl-lower alkyl, heteroaryl-lower alkyl, hydroxy-lower alkyl, halo-lower alkyl, lower alkoxy-lower alkyl, lower alkoxy-lower alkoxy-lower alkyl, halo-lower alkoxy-lower alkyl, lower alkylcarbonyloxy-lower alkyl, arylcarbonyloxy-lower alkyl, aryl-lower alkylcarbonyloxy-lower alkyl, heteroaryl-carbonyloxy-lower alkyl, heteroaryl-lower alkylcarbonyloxy-lower alkyl, lower alkylcarbonyl-lower alkyl, lower alkoxycarbonyl-lower alkyl, arylcarbonyl-lower allkyl, aryl-lower alkylcarbonyl-lower allkyl, aryl-lower alkoxycarbonyl-lower allkyl, cyano-lower alkyl, lower alkylthio-lower alkyl, lower alkylsulfonyl-lower alkyl, aminosulfonyl-lower alkyl, lower alkylaminosulfonyl-lower alkyl, amino-lower alkyl wherein amino is optionally substituted by lower alkyl, di-lower alkyl, lower alkylcarbonyl or lower alkoxycarbonyl; optionally substituted alkenyl, optionally substituted alkinyl; lower alkylthio, arylsulfonyl, heteroarylsulfonyl, lower alkylsulfonyl, aminosulfonyl, lower alkylaminosulfonyl, arylcarbonyl, heteroarylcarbonyl, lower alkylcarbonyl, lower alkoxycarbonyl, aminocarbonyl, lower alkylaminocarbonyl, or carboxy;
$R^3$ is alkyl, hydroxy-lower alkyl, methoxy-lower alkyl, aryl-lower alkyl, heteroaryl-lower alkyl or aryl;
$R^4$ is hydrogen, methyl, hydroxymethyl, trifluoromethyl, hydroxy, methoxy, methylenedioxy, amino, methylamino, dimethylamino, hydroxy-lower alkylamino, acetyl, carboxy, nitro, cyano or halogen; and
$R^5$ is hydrogen, methyl, trifluoromethyl, hydroxy, methoxy, nitro or halogen;
or wherein
$R^1$ is hydrogen,
$R^2$ is lower alkyl, arylsulfonyl, heteroarylsulfonyl, lower alkylsulfonyl, aminosulfonyl, lower alkylaminosulfonyl, arylcarbonyl, heteroarylcarbonyl, lower alkylcarbonyl, lower alkoxycarbonyl, aminocarbonyl, lower alkylaminocarbonyl or carboxy;
$R^3$ is alkyl, hydroxy-lower alkyl, methoxy-lower alkyl, aryl-lower alkyl, or heteroaryl-lower alkyl;
$R^4$ is para-fluoro or para-chloro; and
$R^5$ is hydrogen;
or wherein
$R^1$ is hydrogen,
$R^2$ is lower alkyl, arylsulfonyl, heteroarylsulfonyl, lower alkylsulfonyl, aminosulfonyl, lower alkylaminosulfonyl, arylcarbonyl, heteroarylcarbonyl, lower alkylcarbonyl, lower alkoxycarbonyl, aminocarbonyl, lower alkylaminocarbonyl or carboxy;
$R^3$ is alkyl, hydroxy-lower alkyl, methoxy-lower alkyl, aryl-lower alkyl, heteroaryl-lower alkyl or aryl; and
$R^4$ and $R^5$ are, independently of each other, hydrogen, ortho- or meta-fluoro, ortho- or meta-chloro, ortho- or meta-methoxy, ortho-nitro, ortho-, meta- or para-methyl, or ortho-, meta- or para-hydroxy; and wherein at least one of $R^4$ and $R^5$ is different from hydrogen;
and tautomers and salts thereof.
Furthermore the invention relates to pharmaceutical preparations comprising the compounds mentioned hereinbefore and such compounds wherein $R^1$ is hydrogen and $R^2$, $R^3$, $R^4$ and $R^5$ have any of the indicated meanings, the mentioned compounds and such compounds wherein $R^1$ is hydrogen and $R^2$, $R^3$, $R^4$ and $R^5$ have any of the indicated meanings for use in the treatment of angiogenesis dependent cancers and intraocular neovascular syndromes, methods of treatment of angiogenesis dependent cancers and intraocular neovascular syndromes, and a method of selecting compounds for screening as EphB4 inhibitors by computational procedures.

DETAILED DESCRIPTION OF THE INVENTION

Figure 1:
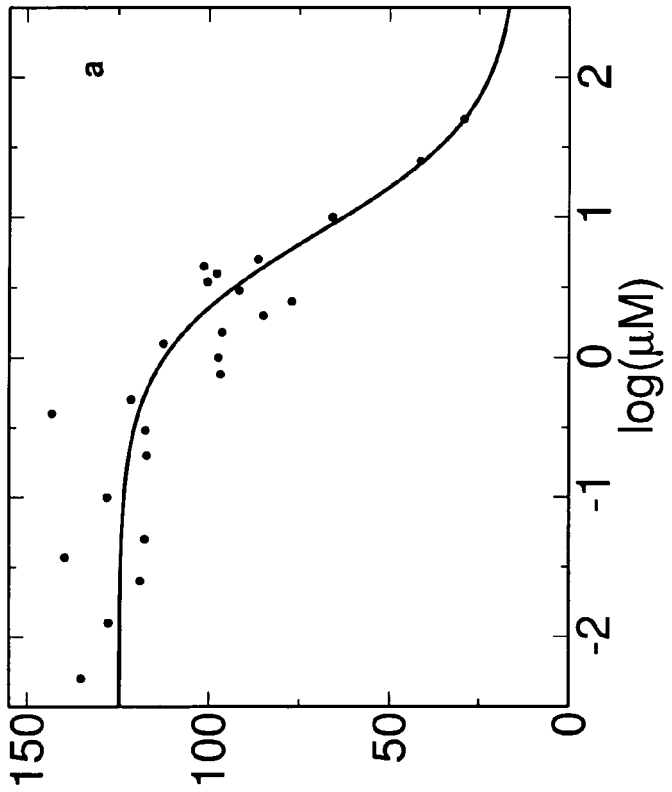
FIG. 1: Plot of the response (arbitrary units) versus the concentration of compound 2 on a logarithmic scale. Data obtained with the Omnia Tyr Recombinant Kit KNZ4051 (Biosource, USA) without (a), and with (b) the addition of detergent (0.01% of Triton X-100). Values in panel (b) were measured in duplicates. The concentration of ATP in both assays was 125 µM, which is close to its $K_m$.
Figure 1:
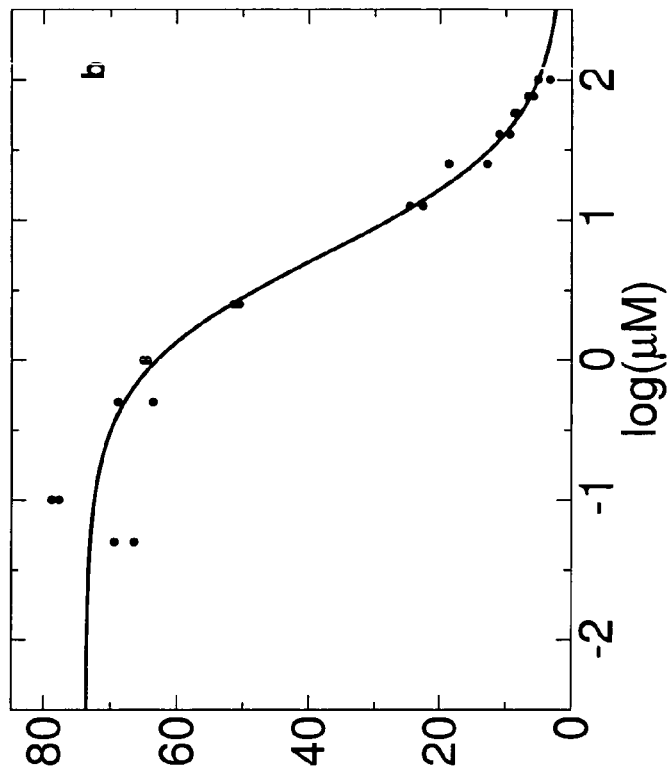

The invention relates to compounds of formula 1

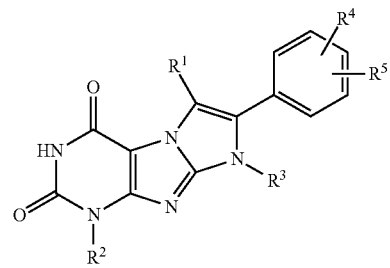

wherein
$R^1$ is alkyl, cycloalkyl, heterocyclyl, aryl-lower alkyl, cycloalkyl-lower alkyl, heteroaryl-lower alkyl, hydroxy-lower alkyl, halo-lower alkyl, lower alkoxy-lower alkyl, lower alkoxy-lower alkoxy-lower alkyl halo-lower alkoxy-lower alkyl, optionally substituted alkenyl, optionally substituted alkinyl, aryl, heteroaryl, hydroxy, lower alkoxy, halo-lower alkoxy, lower alkoxy-lower alkoxy, aryloxy, hetero-aryloxy, formyloxy, lower alkylcarbonyloxy, arylcarbonyloxy, heteroarylcarbonyloxy, sulfhydryl, alkylthio, arylthio, heterarylthio, alkylsulfinyl, arylsulfinyl, heteroarylsulfinyl, alkylsulfonyl, arylsulfonyl, heteroarylsulfonyl, aminosulfonyl, lower alkylaminosulfonyl, amino, unsubstituted or substituted by one or two substitutents selected from lower alkyl, cycloalkyl, aryl-lower alkyl, cycloalkyl-lower alkyl, heteroaryl-lower alkyl, hydroxy-lower alkyl, lower alkoxy-lower alkyl, or substituted by one substituent aryl or heteroaryl and optionally another substituent lower alkyl, or substituted by one substituent formyl, lower alkylcarbonyl, arylcarbonyl, heteroarylcarbonyl, lower alkoxycarbonyl or lower alkoxy-lower alkoxycarbonyl, or wherein the two substituents on nitrogen form together with the nitrogen heterocyclyl;

formyl, lower alkylcarbonyl, arylcarbonyl, heteroarylcarbonyl, carboxy, lower alkoxycarbonyl, lower alkoxy-lower alkoxycarbonyl;

aminocarbonyl and aminothiocarbonyl wherein amino is unsubstituted or substituted by one or two substituents selected from lower alkyl, cycloalkyl, aryl-lower alkyl, cycloalkyl-lower alkyl, heteroaryl-lower alkyl, hydroxy-lower alkyl, lower alkoxy-lower alkyl, or substituted by one substituent aryl or heteroaryl and optionally another substituent lower alkyl, or wherein the two substituents on nitrogen form together with the nitrogen heterocyclyl;

cyano, halogen, or nitro;

$R^2$ is hydrogen, lower alkyl, aryl-lower alkyl, cycloalkyl-lower alkyl, heteroaryl-lower alkyl, hydroxy-lower alkyl, halo-lower alkyl, lower alkoxy-lower alkyl, lower alkoxy-lower alkoxy-lower alkyl, halo-lower alkoxy-lower alkyl, lower alkylcarbonyloxy-lower alkyl, arylcarbonyloxy-lower alkyl, aryl-lower alkylcarbonyloxy-lower alkyl, heteroarylcarbonyloxy-lower alkyl, heteroaryl-lower alkylcarbonyloxy-lower alkyl, lower alkylcarbonyl-lower alkyl, lower alkoxycarbonyl-lower alkyl, arylcarbonyl-lower allkyl, aryl-lower alkylcarbonyl-lower allkyl, aryl-lower alkoxycarbonyl-lower allkyl, cyano-lower alkyl, lower alkylthio-lower alkyl, lower alkylsulfonyl-lower alkyl, aminosulfonyl-lower alkyl, lower alkylaminosulfonyl-lower alkyl, amino-lower alkyl wherein amino is optionally substituted by lower alkyl, di-lower alkyl, lower alkylcarbonyl or lower alkoxycarbonyl, optionally substituted alkenyl, optionally substituted alkinyl; lower alkylthio, arylsulfonyl, heteroarylsulfonyl, lower alkylsulfonyl, aminosulfonyl, lower alkylaminosulfonyl, arylcarbonyl, heteroarylcarbonyl, lower alkylcarbonyl, lower alkoxycarbonyl, aminocarbonyl, lower alkylaminocarbonyl or carboxy;

$R^3$ is alkyl, hydroxy-lower alkyl, methoxy-lower alkyl, aryl-lower alkyl, heteroaryl-lower alkyl or aryl;

$R^4$ is hydrogen, methyl, hydroxymethyl, trifluoromethyl, hydroxy, methoxy, methylenedioxy, amino, methylamino, dimethylamino, hydroxy-lower alkylamino, acetyl, carboxy, nitro, cyano or halogen; and $R^5$ is hydrogen, methyl, trifluoromethyl, hydroxy, methoxy, nitro or halogen;

and tautomers and salts thereof.

Furthermore, the invention relates to compounds of formula 1 wherein $R^1$ is hydrogen, $R^2$ is lower alkyl, arylsulfonyl, heteroarylsulfonyl, lower alkylsulfonyl, aminosulfonyl, lower alkylaminosulfonyl, arylcarbonyl, heteroarylcarbonyl, lower alkylcarbonyl, lower alkoxycarbonyl, aminocarbonyl, lower alkylaminocarbonyl or carboxy;

$R^3$ is alkyl, hydroxy-lower alkyl, methoxy-lower alkyl, aryl-lower alkyl, or heteroaryl-lower alkyl;

$R^4$ is para-fluoro or para-chloro; and $R^5$ is hydrogen;

or wherein $R^1$ is hydrogen, $R^2$ is lower alkyl, arylsulfonyl, heteroarylsulfonyl, lower alkylsulfonyl, aminosulfonyl, lower alkylaminosulfonyl, arylcarbonyl, heteroarylcarbonyl, lower alkylcarbonyl, lower alkoxycarbonyl, aminocarbonyl, lower alkylaminocarbonyl or carboxy;

$R^3$ is alkyl, hydroxy-lower alkyl, methoxy-lower alkyl, aryl-lower alkyl, heteroaryl-lower alkyl or aryl; and $R^4$ and $R^5$ are, independently of each other, hydrogen, ortho- or meta-fluoro, ortho- or meta-chloro, ortho- or meta-methoxy, ortho-nitro, ortho-, meta- or para-methyl, or ortho-, meta- or para-hydroxy; and wherein at least one of $R^4$ and $R^5$ is different from hydrogen;

and tautomers and salts thereof.

The invention relates to possible tautomers of the compounds of formula 1. Examples of tautomers are those wherein the double bond(s) is(are) in a different position of the ring(s), the proton(s) located on nitrogen atoms of the rings are on other nitrogen atoms or on adjacent carbonyl oxygen, i.e. wherein a formal amide function of the six-membered heterocyclic ring is in its hydroxy-imino or α-hydroxy-enamine tautomeric form, or the protons of substituent $R^1$ is located at a ring nitrogen atom, i.e. wherein the formal α-$R^1$-enamine function is in the corresponding amide, thioamide or amidino form or the proton of $R^1$ further delocalized in the rings.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Alkyl has from 1 to 12, preferably from 1 to 7 carbon atoms, and is linear or branched. Alkyl is preferably lower alkyl.

Lower alkyl has 1 to 4 carbon atoms and is butyl, such as n-butyl, sec-butyl, isobutyl, tert-butyl, propyl, such as n-propyl or isopropyl, ethyl or methyl. Preferably lower alkyl is methyl or ethyl.

Cycloalkyl has preferably 3 to 7 ring carbon atoms, and may be unsubstituted or substituted, e.g. by lower alkyl or lower alkoxy. Cycloalkyl is, for example, cyclohexyl, cyclopentyl, methylcyclopentyl, or cyclopropyl.

Aryl stands for a mono- or bicyclic fused ring aromatic group with 5 to 10 carbon atoms, such as optionally substituted phenyl, 1-naphthyl or 2-naphthyl, or also a partially saturated bicyclic fused ring comprising a phenyl group, such as indanyl, dihydro- or tetrahydronaphthyl.

In optionally substituted phenyl, phenyl carries one, two or three substituents, preferably one or two substituents, and substituents are preferably lower alkyl, lower alkoxy, lower alkoxy-lower alkoxy, methylenedioxy, hydroxy-lower alkyl, halo-lower alkyl, lower alkoxy-lower alkyl, halo, cyano, or nitro, in particular lower alkyl, lower alkoxy, halo-lower alkyl and halo.

Heteroaryl represents an aromatic group containing at least one heteroatom selected from nitrogen, oxygen and sulfur, and is mono- or bicyclic. Monocyclic heteroaryl includes 5 or 6 membered heteroaryl groups containing 1, 2, 3 or 4 heteroatoms selected from nitrogen, sulfur and oxygen. Bicyclic heteroaryl includes 9 or 10 membered fused-ring heteroaryl groups. Examples of heteroaryl include optionally substituted pyrrolyl, thienyl, furyl, pyrazolyl, imidazolyl, triazolyl, oxazolyl, isoxazolyl, oxadiazolyl, thiazolyl, isothiazolyl, thiadiazolyl, pyridyl, pyridazinyl, pyrimidinyl, pyrazinyl, benzo fused derivatives of such monocyclic heteroaryl groups, such as indolyl, benzimidazolyl or benzofuryl, quinolinyl, isoquinolinyl, quinazolinyl, or purinyl. In particular, heteroaryl is pyrrolyl, thienyl, furyl, pyrazolyl, imidazolyl, triazolyl, pyridyl, indolyl, or benzimidazolyl, preferably pyridyl, such as 2-, 3- or 4-pyridyl.

In optionally substituted heteroaryl, substituents are preferably lower alkyl, lower alkoxy, lower alkoxy-lower alkoxy, amino, optionally substituted by one or two substituents selected from lower alkyl, lower alkenyl and alkylcarbonyl, hydroxy-lower alkyl, halo-lower alkyl, lower alkoxy-lower alkyl, halo, cyano, or nitro.

Hydroxy-lower alkyl is preferably hydroxymethyl, 2-hydroxyethyl, 2-hydroxy-2-propyl or 4-hydroxybutyl.

Halogen is fluorine, chlorine, bromine, or iodine, preferably fluorine or chlorine.

Halo-lower alkyl is preferably fluoro-lower alkyl, especially trifluoromethyl, 3,3,3-trifluoro-ethyl or pentafluoroethyl.

Cyano-lower alkyl designates preferably cyanomethyl and cyanoethyl.

Lower alkoxy is especially methoxy, ethoxy, isopropyloxy, or tert-butyloxy.

Aryl-lower alkyl includes aryl and lower alkyl as defined hereinbefore, and is e.g. benzyl, 1-phenethyl or 2-phenethyl.

Heteroaryl-lower alkyl includes heteroaryl and lower alkyl as defined hereinbefore, and is e.g. 2-, 3- or 4-pyridylmethyl, 1- or 2-pyrrolylmethyl, 1-pyrazolylmethyl, 1-imidazolylmethyl, 2-(1-imidazolyl)ethyl or 3-(1-imidazolyl)propyl, preferably 2-, 3- or 4-pyridylmethyl.

Alkenyl contains one or more, e.g. two or three, double bonds, and is preferably lower alkenyl, such as 1- or 2-butenyl, 3-methyl-2-butenyl, 1-propenyl, 2-methyl-2-propenyl, allyl or vinyl.

Alkinyl is preferably lower alkinyl, such as propargyl or acetylenyl.

In optionally substituted alkenyl or alkinyl, substituents are preferably lower alkyl, lower alkoxy, lower alkoxycarbonyl, halo, aryl or heteroaryl, and are connected with a saturated or unsaturated carbon atom of alkenyl or alkinyl.

Heterocyclyl designates preferably a saturated, partially saturated or unsaturated, mono- or bicyclic ring containing 4-10 atoms comprising one, two or three heteroatoms selected from nitrogen, oxygen and sulfur, which may, unless otherwise specified, be carbon or nitrogen linked, wherein a ring nitrogen atom may optionally be substituted by a group selected from lower alkyl, amino-lower alkyl, aryl, aryl-lower alkyl and lower alkylcarbonyl, and a ring carbon atom may be substituted by lower alkyl, amino-lower alkyl, aryl, aryl-lower alkyl, heteroaryl, lower alkoxy, hydroxy or oxo. Examples of heterocyclyl are pyrrolidinyl, oxazolidinyl, thiazolidinyl, piperidinyl, morpholinyl, piperazinyl, dioxolanyl, tetrahydrofuranyl and tetrahydropyranyl, in particular pyrrolidinyl, piperidinyl, and morpholinyl.

In formula 1 the bond connecting substituent $R^4$ and $R^5$, respectively, with the phenyl group is not connected with a particular carbon atom of the phenyl ring. The meaning of such a formula is that substituent $R^4$ and $R^5$, respectively, can be connected to the ortho, meta or para position of the phenyl ring, independently of each other. This means that substituents $R^4$ and $R^5$ may be located in ortho/ortho, ortho/meta, ortho/para, meta/ortho, meta/meta, meta/para, para/ortho or para/meta position. If $R^5$ is hydrogen, $R^4$ is in ortho, meta or para position, e.g. in para position. If both $R^4$ and $R^5$ are different from hydrogen, $R^4$ and $R^5$ are, e.g., in ortho/para, meta/meta or para/ortho position.

Salts are especially the pharmaceutically acceptable salts of compounds of formula 1.

Such salts are formed, for example, as acid addition salts, preferably with organic or inorganic acids, from compounds of formula 1 with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, glycolic acid, lactic acid, malic acid, tartaric acid, or citric acid. Salts are also formed, for example, as salts with organic or inorganic bases, from compounds of formula 1 with a nitrogen atom bearing an acidic hydrogen. Examples of suitable cations are sodium, potassium, calcium or magnesium cations, or cations of organic nitrogen bases, e.g. protonated mono-, di- or tri-(2-hydroxyethyl)amine.

In view of the close relationship between the novel compounds in free form and those in the form of their salts, any reference to the free compounds hereinbefore and hereinafter is to be understood as referring also to the corresponding salts, as appropriate and expedient. Likewise, in view of the close relationship between the novel compounds as shown in formula 1 and their tautomers, any reference to the compounds of formula 1 is to be understood as referring also to the corresponding tautomers.

The compounds of formula 1 have valuable pharmacological properties. The invention also relates to compounds of formula 1 as defined hereinbefore for use as medicaments. Compounds of the formula 1 inhibit Ephrin receptor kinase, in particular EphB4 kinase, are modulating angiogenesis, and are especially appropriate for the use against diseases or disorders such as angiogenesis dependent cancers, intraocular neovascular syndromes and related diseases, e.g. psoriasis and rheumathoid arthritis. Angiogenesis dependent cancers are, for example, so-called solid tumors, especially cancers of the gastrointestinal tract, the pancreas, breast, stomach, cervix, bladder, kidney, prostate, ovaries, endometrium, lung, brain, melanoma, Kaposi's sarcoma, squamous cell carcinoma of head and neck, malignant pleural mesotherioma, lymphoma or multiple myeloma, also haemangioblastoma and haemangioma, and further liquid tumors, e.g. leukemias. Intraocular neovascular syndromes are e.g. diabetic retinopathy, neovascular glaucoma, ischemic retinopathies and macula degeneration, e.g. age related macula degeneration. Other angiogenesis related diseases are restenosis, e.g. stent-induced restenosis, Crohn's disease, and Hodgkin's disease.

In particular the invention relates to compounds of formula 1, wherein $R^1$ is lower alkyl, hydroxy-lower alkyl, hydroxy, lower alkoxy, sulfhydryl, lower alkylthio, lower alkylsulfonyl, aminosulfonyl, lower alkylaminosulfonyl, amino, unsubstituted or substituted by one or two substitutents selected from lower alkyl, cycloalkyl, optionally substituted phenyl-lower alkyl, cycloalkyl-lower alkyl, pyridyl-, pyrrolyl-, pyrazolyl- or imidazolyl-lower alkyl, hydroxy-lower alkyl, lower alkoxy-lower alkyl, or substituted by one substituent optionally substituted phenyl and optionally another substituent lower alkyl, or substituted by one substituent formyl, lower alkylcarbonyl, optionally substituted phenylcarbonyl, lower alkoxycarbonyl or lower alkoxy-lower alkoxycarbonyl, or wherein the two substituents on nitrogen form together with the nitrogen heterocyclyl;

lower alkylcarbonyl, carboxy, lower alkoxycarbonyl, lower alkoxy-lower alkoxycarbonyl;

aminocarbonyl and aminothiocarbonyl wherein amino is unsubstituted or substituted by one or two substitutents selected from lower alkyl, cycloalkyl, optionally substituted phenyl-lower alkyl, cycloalkyl-lower alkyl, pyridyl-, pyrrolyl-, pyrazolyl- or imidazolyl-lower alkyl, hydroxy-lower alkyl, lower alkoxy-lower alkyl, or substituted by one substituent optionally substituted phenyl and optionally another substituent lower alkyl, or wherein the two substituents on nitrogen form together with the nitrogen heterocyclyl; cyano, halogen, or nitro.

More preferred are compounds wherein $R^1$ is lower alkyl, hydroxy-lower alkyl, hydroxy, sulfhydryl, lower alkylthio, lower alkylsulfonyl, aminosulfonyl, lower alkylaminosulfonyl, amino, unsubstituted or substituted by lower alkyl, di-lower alkyl, lower alkylcarbonyl, lower alkoxycarbonyl, or lower alkoxy-lower alkoxycarbonyl; lower alkylcarbonyl; aminocarbonyl and aminothiocarbonyl wherein amino is unsubstituted or substituted by lower alkyl or di-lower alkyl; cyano, halogen, or nitro.

Even more preferred are compounds wherein $R^1$ is lower alkyl, lower alkylthio, lower alkylsulfonyl, aminosulfonyl, lower alkylaminosulfonyl, amino, aminocarbonyl or aminothiocarbonyl.

Likewise preferred are compounds wherein $R^1$ is hydroxy, halogen, sulfhydryl, amino, aminocarbonyl, aminothiocarbonyl or lower alkylamino.

In particular the invention relates to compounds of formula 1, wherein $R^2$ is hydrogen, lower alkyl, optionally substituted phenyl-lower alkyl, lower alkylcarbonyloxy-lower alkyl, lower alkylcarbonyl-lower alkyl, lower alkoxycarbonyl-lower alkyl, lower alkylthio-lower alkyl, lower alkylsulfonyl-lower alkyl, aminosulfonyl-lower alkyl, lower alkylaminosulfonyl-lower alkyl, amino-lower alkyl wherein amino is optionally substituted by lower alkyl, di-lower alkyl, lower alkylcarbonyl or lower alkoxycarbonyl; optionally substituted alkenyl, optionally substituted alkinyl; lower alkylthio, optionally substituted phenylsulfonyl, optionally substituted pyridylsulfonyl, lower alkylsulfonyl, aminosulfonyl, lower alkylamino-sulfonyl, optionally substituted phenylcarbonyl, optionally substituted pyridylcarbonyl, lower alkylcarbonyl, lower alkoxycarbonyl, aminocarbonyl, lower alkylaminocarbonyl, or carboxy.

More preferred are compounds wherein $R^2$ is lower alkyl, optionally substituted phenyl-lower alkyl, lower alkylcarbonyloxy-lower alkyl, lower alkylcarbonyl-lower alkyl, lower alkoxycarbonyl-lower alkyl, lower alkylthio-lower alkyl, lower alkylsulfonyl-lower alkyl, aminosulfonyl-lower alkyl, lower alkylaminosulfonyl-lower alkyl, amino-lower alkyl wherein amino is optionally substituted by lower alkyl, di-lower alkyl, lower alkylcarbonyl or lower alkoxycarbonyl; optionally substituted phenylsulfonyl, optionally substituted pyridylsulfonyl, lower alkylsulfonyl, optionally substituted phenylcarbonyl, optionally substituted pyridyl-carbonyl, lower alkylcarbonyl, lower alkoxycarbonyl, aminocarbonyl, or carboxy.

Even more preferred are compounds wherein $R^2$ is lower alkyl, optionally substituted phenyl-lower alkyl, lower alkylcarbonyloxy-lower alkyl, lower alkylcarbonyl-lower alkyl, lower alkoxycarbonyl-lower alkyl, lower alkylthio-lower alkyl, lower alkylsulfonyl-lower alkyl, aminosulfonyl-lower alkyl, lower alkylaminosulfonyl-lower alkyl, or amino-lower alkyl.

Likewise preferred are compounds wherein $R^2$ optionally substituted phenylsulfonyl, optionally substituted pyridylsulfonyl, lower alkylsulfonyl, optionally substituted phenylcarbonyl, optionally substituted pyridylcarbonyl, lower alkylcarbonyl, lower alkoxycarbonyl, aminocarbonyl, or carboxy.

In particular the invention relates to compounds of formula 1, wherein $R^3$ is lower alkyl, hydroxy-lower alkyl, methoxy-lower alkyl, optionally substituted phenyl-lower alkyl, pyridyl-, pyrrolyl-, pyrazolyl- or imidazolyl-lower alkyl, or optionally substituted phenyl.

More preferred are compounds wherein $R^3$ is lower alkyl, hydroxy-lower alkyl, methoxy-lower alkyl, phenyl-lower alkyl, pyridyl-lower alkyl, or phenyl optionally substituted by one or two substituents lower alkyl, lower alkoxy, halo-lower alkyl or halo.

Even more preferred are compounds wherein $R^3$ is lower alkyl, hydroxy-lower alkyl, methoxy-lower alkyl, or phenyl optionally substituted by one or two substituents lower alkyl or lower alkoxy.

Likewise preferred are compounds wherein $R^3$ is lower alkyl, optionally substituted phenyl-lower alkyl, or pyridyl-, pyrrolyl-, pyrazolyl- or imidazolyl-lower alkyl.

In particular the invention relates to compounds of formula 1, wherein
$R^4$ is hydrogen, methyl, trifluoromethyl, hydroxymethyl, hydroxy, methoxy, methylenedioxy, acetyl, nitro, cyano, or halogen; and
$R^5$ is hydrogen, methyl, trifluoromethyl, hydroxy, methoxy, nitro, or halogen.

More preferred are compounds wherein
$R^4$ and $R^5$ are, independently of each other, hydrogen, methyl, hydroxy, methoxy, nitro, chloro or fluoro.

Likewise preferred are compounds wherein
$R^4$ is hydrogen, methyl, trifluoromethyl, methoxy, acetyl, nitro, cyano or halogen; and
$R^5$ is hydrogen, methyl, trifluoromethyl or halogen.

More particularly, the invention relates to compounds of formula 1, wherein
$R^1$ is hydroxy, halogen, sulfhydryl, amino, aminocarbonyl, aminothiocarbonyl or lower alkylamino;
$R^2$ is arylsulfonyl, heteroarylsulfonyl, lower alkylsulfonyl, arylcarbonyl, heteroarylcarbonyl, lower alkylcarbonyl, lower alkoxycarbonyl, aminocarbonyl or carboxy;
$R^3$ is alkyl, aryl-lower alkyl or heteroaryl-lower alkyl;
$R^4$ is hydrogen, methyl, trifluoromethyl, methoxy, acetyl, nitro, cyano or halogen; and
$R^5$ is hydrogen, methyl, trifluoromethyl or halogen.

Even more particularly, the invention relates to compounds of formula 1, wherein
$R^1$ is hydroxy, halogen, sulfhydryl, amino or lower alkylamino;
$R^2$ is arylsulfonyl, heteroarylsulfonyl, lower alkylsulfonyl, arylcarbonyl, heteroarylcarbonyl, lower alkylcarbonyl, loweralkoxycarbonyl, aminocarbonyl or carboxy;
$R^3$ is alkyl, aryl-lower alkyl or heteroaryl-lower alkyl;
$R^4$ is hydrogen, methyl, trifluoromethyl, methoxy, acetyl, nitro, cyano or halogen; and
$R^5$ is hydrogen, methyl, trifluoromethyl or halogen.

More particularly, the invention relates to compounds of formula 1, wherein $R^1$ is hydroxy or amino; and $R^2$ to $R^5$ have the indicated meanings; and
to compounds of formula 1, wherein $R^2$ is arylsulfonyl, methylcarbonyl or carboxy; and $R^1$ and $R^3$ to $R^5$ have the indicated meanings; and
to compounds of formula 1, wherein $R^3$ is alkyl; and $R^1$, $R^2$, $R^4$ and $R^5$ have the indicated meanings; and
to compounds of formula 1, wherein $R^4$ is fluorine or chlorine, and $R^1$ to $R^3$ and $R^5$ have the indicated meanings; and
to compounds of formula 1, wherein $R^5$ is hydrogen, and $R^1$ to $R^4$ have the indicated meanings.

Most preferred are compounds of formula 1, wherein $R^1$ is hydroxy or amino; $R^2$ is arylsulfonyl, methylcarbonyl or carboxy; $R^3$ is alkyl; $R^4$ is fluorine or chlorine; and $R^5$ is hydrogen.

Particularly preferred are the compounds of the examples.

Some compounds of formula 1, wherein $R^1$ is hydrogen, may already be known in the prior art, although they have never been used as compounds for the treatment of angiogenesis dependent cancers and intraocular neovascular syndromes. The invention therefore relates to compounds of formula 1

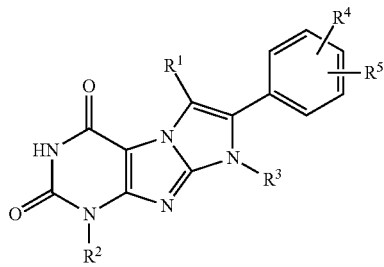

wherein
$R^1$ is hydrogen, alkyl, cycloalkyl, heterocyclyl, aryl-lower alkyl, cycloalkyl-lower alkyl, heteroaryl-lower alkyl, hydroxy-lower alkyl, halo-lower alkyl, lower alkoxy-lower alkyl, lower alkoxy-lower alkoxy-lower alkyl, halo-lower alkoxy-lower alkyl, optionally substituted alkenyl, optionally substituted alkinyl, aryl, heteroaryl, hydroxy, lower alkoxy, halo-lower alkoxy, lower alkoxy-lower alkoxy, aryloxy, hetero-aryloxy, formyloxy, lower alkylcarbonyloxy, arylcarbonyloxy, heteroarylcarbonyloxy, sulfhydryl, alkylthio, arylthio, heterarylthio, alkylsulfinyl, arylsulfinyl, heteroarylsulfinyl, alkylsulfonyl, arylsulfonyl, heteroarylsulfonyl, aminosulfonyl, lower alkylaminosulfonyl, amino, unsubstituted or substituted by one or two substitutents selected from lower alkyl, cycloalkyl, aryl-lower alkyl, cycloalkyl-lower alkyl, heteroaryl-lower alkyl, hydroxy-lower alkyl, lower alkoxy-lower alkyl, or substituted by one substituent aryl or heteroaryl and optionally another substituent lower alkyl, or substituted by one substituent formyl, lower alkylcarbonyl, arylcarbonyl, heteroarylcarbonyl, lower alkoxycarbonyl or lower alkoxy-lower alkoxycarbonyl, or wherein the two substituents on nitrogen form together with the nitrogen heterocyclyl;
formyl, lower alkylcarbonyl, arylcarbonyl, heteroarylcarbonyl, carboxy, lower alkoxycarbonyl, lower alkoxy-lower alkoxycarbonyl;
aminocarbonyl and aminothiocarbonyl wherein amino is unsubstituted or substituted by one or two substitutents selected from lower alkyl, cycloalkyl, aryl-lower alkyl, cycloalkyl-lower alkyl, heteroaryl-lower alkyl, hydroxy-lower alkyl, lower alkoxy-lower alkyl, or substituted by one substituent aryl or heteroaryl and optionally another substituent lower alkyl, or wherein the two substituents on nitrogen form together with the nitrogen heterocyclyl;
cyano, halogen, or nitro;
$R^2$ is hydrogen, lower alkyl, aryl-lower alkyl, cycloalkyl-lower alkyl, heteroaryl-lower alkyl, hydroxy-lower alkyl, halo-lower alkyl, lower alkoxy-lower alkyl, lower alkoxy-lower alkoxy-lower alkyl, halo-lower alkoxy-lower alkyl, lower alkylcarbonyloxy-lower alkyl, arylcarbonyloxy-lower alkyl, aryl-lower alkylcarbonyloxy-lower alkyl, heteroaryl-carbonyloxy-lower alkyl, heteroaryl-lower alkylcarbonyloxy-lower alkyl, lower alkylcarbonyl-lower alkyl, lower alkoxycarbonyl-lower alkyl, arylcarbonyl-lower allkyl, aryl-lower alkylcarbonyl-lower allkyl, aryl-lower alkoxycarbonyl-lower allkyl, cyano-lower alkyl, lower alkylthio-lower alkyl, lower alkylsulfonyl-lower alkyl, aminosulfonyl-lower alkyl, lower alkylaminosulfonyl-lower alkyl, amino-lower alkyl wherein amino is optionally substituted by lower alkyl, di-lower alkyl, lower alkylcarbonyl or lower alkoxycarbonyl, optionally substituted alkenyl, optionally substituted alkinyl; lower alkylthio, arylsulfonyl, heteroarylsulfonyl, lower alkylsulfonyl, aminosulfonyl, lower alkylaminosulfonyl, arylcarbonyl, heteroarylcarbonyl, lower alkylcarbonyl, lower alkoxycarbonyl, aminocarbonyl, lower alkylaminocarbonyl or carboxy;
$R^3$ is alkyl, hydroxy-lower alkyl, methoxy-lower alkyl, aryl-lower alkyl, heteroaryl-lower alkyl or aryl;
$R^4$ is hydrogen, methyl, hydroxymethyl, trifluoromethyl, methoxy, methylenedioxy, acetyl, nitro, cyano or halogen; and
$R^5$ is hydrogen, methyl, trifluoromethyl or halogen;
and tautomers and salts thereof;
in particular compounds of formula 1 wherein
$R^1$ is hydrogen, hydroxy, halogen, sulfhydryl, amino, aminocarbonyl, aminothiocarbonyl or lower alkylamino;
$R^2$ is lower alkyl, arylsulfonyl, heteroarylsulfonyl, lower alkylsulfonyl, arylcarbonyl, heteroarylcarbonyl, lower alkylcarbonyl, lower alkoxycarbonyl, aminocarbonyl or carboxy;
$R^3$ is alkyl, hydroxy-lower alkyl, methoxy-lower alkyl, aryl-lower alkyl, heteroaryl-lower alkyl or aryl;
$R^4$ is hydrogen, methyl, trifluoromethyl, methoxy, methylenedioxy, acetyl, nitro, cyano or halogen; and
$R^5$ is hydrogen, methyl, trifluoromethyl or halogen;
and tautomers and salts thereof;
for use in the treatment of angiogenesis dependent cancers and intraocular neovascular syndromes.

In particular, the invention relates to compounds of formula 1, wherein $R^1$ is hydrogen; $R^2$ is lower alkyl; $R^3$ is alkyl, hydroxy-lower alkyl, methoxy-lower alkyl, aryl-lower alkyl, heteroaryl-lower alkyl or aryl; and $R^4$ and $R^5$ are hydrogen;
for use in the treatment of angiogenesis dependent cancers and intraocular neovascular syndromes.

More particularly, the invention relates to compounds of formula 1, wherein $R^1$ is hydrogen; $R^2$ is methyl; $R^3$ is lower alkyl or hydroxy-lower alkyl; and $R^4$ and $R^5$ are hydrogen;
for use in the treatment of angiogenesis dependent cancers and intraocular neovascular syndromes.

Most preferred, the invention relates to the compounds of the examples for use in the treatment of angiogenesis dependent cancers and intraocular neovascular syndromes.

Furthermore the invention relates to pharmaceutical preparations comprising the compounds mentioned hereinbefore as active ingredient and that can be used especially in the treatment of the diseases mentioned. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention relates especially to pharmaceutical compositions that comprise a compound of formula 1, a tautomer, or a pharmaceutically acceptable salt, or a hydrate or solvate thereof, and at least one pharmaceutically acceptable carrier.

A pharmaceutical composition for the treatment of angiogenesis dependent cancers and intraocular neovascular syndromes of a warm-blooded animal, especially a human requiring such treatment, comprising a compound of formula 1 as active ingredient in a quantity that is therapeutically active against the said diseases, is likewise preferred.

The pharmaceutical compositions comprise from approximately 1% to approximately 95% active ingredient. Unit dose forms are, for example, coated and uncoated tablets, ampoules, vials, suppositories, or capsules. Further dosage forms are, for example, ointments, creams, pastes, foams, tinctures, lip-sticks, drops, sprays, dispersions, etc. Examples are capsules containing from about 0.05 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms. The alcohol component of these fatty acid esters has a maximum of 6 carbon atoms and is a monovalent or polyvalent, for example a mono-, di- or trivalent, alcohol, especially glycol and glycerol. As mixtures of fatty acid esters, vegetable oils such as cottonseed oil, almond oil, olive oil, castor oil, sesame oil, soybean oil and groundnut oil are especially useful.

The manufacture of injectable preparations is usually carried out under sterile conditions, as is the filling, for example, into ampoules or vials, and the sealing of the containers.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the abovementioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinyl-pyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropyl-methylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxy-ethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration, aqueous solutions of an active ingredient in water-soluble form or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents. Solutions such as are used, for example, for parenteral administration can also be employed as infusion solutions.

Preferred preservatives are, for example, antioxidants, such as ascorbic acid, or microbicides, such as sorbic acid or benzoic acid.

Furthermore the invention relates to a method of treatment of angiogenesis dependent cancers and intraocular neovascular syndromes in a patient in need thereof, characterized in that a therapeutically effective amount of a compound of formula 1 as described hereinbefore as such or in form of a pharmaceutical preparation comprising it is administered to the patient in need thereof.

The compounds of formula 1 can be administered as such or especially in the form of pharmaceutical compositions, preferably in an amount effective against the said diseases, to a warm-blooded animal, for example a human, requiring such treatment. In the case of an individual having a bodyweight of about 70 kg the daily dose administered is from approximately 0.05 g to approximately 5 g, preferably from approximately 0.25 g to approximately 1.5 g, of a compound of the present invention.

Furthermore the invention relates to a method of selecting compounds for screening as target inhibitors by computational procedures, in particular for the target EphB4.

The method of the invention termed ALTA (anchor-based library tailoring) starts from a large pool of compounds and consists of six steps which are illustrated in Scheme 1. The statistics of the application to EphB4 is shown in Table 1. It is important to underline that although a suite of in-house developed software was used in the present study, the basic workflow can be reproduced with any combination of software that is capable of carrying out all the steps.

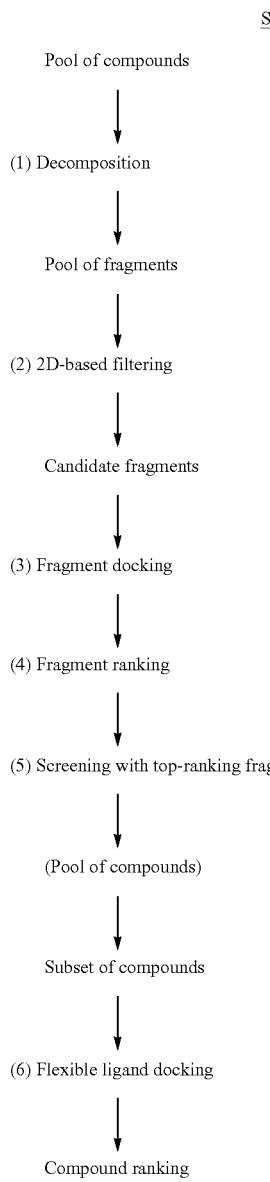

Scheme 1

The pool of compounds, to which the method is applied, may be derived by any method. In the particular example, three libraries were combined for a total of 728,202 compounds: the NCI database, the ChemDiv library (Moscow, Russia) and the synthetic and natural compound library of InterBioScreen (Moscow, Russia).

In step 1 of ALTA, the compounds are decomposed using the program DAIM into predominantly rigid fragments by automatic identification and cutting of rotatable bonds (Kolb P. and Caflisch A., J Med Chem 2006, 49:7384-7392). The decomposition of a molecule proceeds in four phases: ring identification, initial fragment definition, functional group merging, and completion of the valences. (i) Rings are identified by successively enumerating all neighbours (i.e., directly covalently bound atoms) of every atom, similar to a breadth-first search. A neighbour with an already assigned number indicates a ring closure, and the corresponding ring size is the sum of the two numbers. (ii) A fragment is defined as a set of atoms connected by unbreakable bonds. The basic definition of unbreakable bonds includes terminal, double, triple, and aromatic bonds and bonds in rings. Nonrotatable and unbreakable bonds are distinguished in DAIM; a nonrotatable bond is always unbreakable, whereas the reverse is not true (e.g., a double bond is nonrotatable and unbreakable, whereas an amide bond is unbreakable but can assume more than one conformation). An extended definition of unbreakable bonds is used since with the basic definition mentioned above single bonds of groups that form chemical entities would be cut (e.g., in a sulfonamide group, the bond between sulfur and nitrogen is formally a single bond and would thus be cut). This extended list includes amide, phosphate group, and sulfonamide bonds, as well as the single bonds in conjugated systems, and the single bond connecting an amidine group. (iii) To form chemically relevant fragments and avoid the generation of many small groups, small functional groups (e.g., —OH, —CH$_3$, —CX$_3$ [where X can be any halogen], —SO$_3$, —CHO, —NO$_2$, —NH$_2$ and —SH) are merged with the fragment they are connected to. Unbreakable bonds and functional groups (points ii and iii, respectively) can be defined by the user. (iv) In the final step, missing atom neighbours are added. An atom will lack a neighbour atom where the bond connecting them has been cut. These missing neighbours are replaced by hydrogen atoms to reconstitute the correct valence for every atom. A methyl group is used to fill valences where a hydrogen atom would result in an unwanted additional hydrogen bond direction (e.g., a hydrogen replacing a carbon atom bound to an sp$^3$ nitrogen).

Finally, the three fragments with the highest chemical richness (sum over the entries in the DAIM molecular fingerprint) are selected for every compound.

In step 2, candidate anchors are chosen from the set of unique fragments, which fulfil the constraints imposed by the binding site. For the particular example of EphB4 binding, the presence of both hydrogen bond donor and acceptor, i.e., the ability of a fragment to form the characteristic bidentate hydrogen bonds of ATP with the hinge region of a kinase is used.

In step 3, fragments that contain at least one ring, one hydrogen bond donor (nitrogen, oxygen or sulfur connected to a hydrogen) and one acceptor (nitrogen with a lone pair or oxygen) are docked with a rigid-fragment docking program, e.g. SEED (Majeux N. et al., Proteins: Structure, Function and Genetics 1999, 37:88-105; 2001 42:256-268). SEED docks polar fragments in positions of the receptor where at least one hydrogen bond with good geometry is made. First, predefined rules allow the distribution of vectors of unitary length on all H-bond groups of the fragment in a direction for an ideal H-bond geometry. For example, if a nitrogen atom is bound to two heavy atoms, one H-bond vector is generated in the direction of either the lone pair or the NH bond. The same procedure is then used for the polar groups in the receptor binding site. To discard receptor vectors that point into a region of space occupied by other atoms of the protein and select preferentially vectors in the concave regions of the receptor, a spherical probe is set on the vector extremity at a distance corresponding to the sum of the van der Waals radii of the acceptor or donor atom and the probe. The van der Waals interaction between the probe and all the receptor atoms is then evaluated except for the receptor hydrogen atom involved in the H-bond. The vectors which show less favourable van der Waals energies are discarded. Finally, the docking itself is achieved by matching a H-bond vector of the receptor with a H-bond vector of the fragment at a distance that depends on the atom types of donor and acceptor involved in the hydrogen bond. The fragment is then rotated around the H-bond axis to increase sampling. The presence of a ring is required to select only fragments with a certain rigidity and thus fixed relative orientation of the donor and acceptor group(s). Docked fragments are considered to form the bidentate hydrogen bonds if a matching donor and acceptor is found within a radius of 3 Å around the carbonyl oxygen of Glu694 and the amide nitrogen of Met696, respectively. Glu694 and Met696 are the first and last residue in the hinge region of EphB4.

In step 4, these fragments are ranked according to their binding energy, which is the sum of van der Waals interaction, electrostatic desolvation of both the receptor and the fragment and the screened electrostatic interaction calculated with a continuum model of the solvent. There are no terms reflecting the internal energy, since fragments are treated as rigid.

In step 5, using the 1,205 top-ranking fragments as queries, 21,418 compounds are retrieved from the composite library of 728,202 molecules.

Finally, in step 6, the program FFLD is used for fragment-based flexible-ligand docking by genetic algorithm optimization (Majeux N. et al., Proteins: Structure, Function and Genetics 1999, 37:88-105; 2001 42:256-268). In the particular example of EphB4, the protein is kept rigid during docking, but two structures with different orientations of the hydroxy group of Thr693 are used for both fragment and compound docking, since the two positions of the hydrogen are equally probable according to the criteria which are applied during model building.

TABLE 1

Application of the ALTA approach to the EphB4 kinase

| Step | Outcome | $N_{mol}$[a] |
|---|---|---|
| | original library | 728'202 |
| (1) | fragments obtained by decomposition | 35'513 |
| (2) | fragments remaining after 2D-based filtering | 13'533 |
| (3) | fragments forming two hydrogen bonds with hinge | 5'235 |
| (4) | anchor fragments selected upon energy ranking | 1'205 |
| (5)(6) | molecules docked using the "mis"[b] | 21'418 |
| (5)(6) | molecules docked using the "mds"[c] | 8'849 |
| (6) | molecules forming one or two hydrogen bonds with hinge | 9'960 |

[a] Number of fragments/compounds processed in individual steps. Docking (steps 3 and 6) is carried out in parallel on two structures of EphB4 differing only in the orientation of the hydroxy group of Thr693 in the ATP binding site. The value of $N_{mol}$ is the number of unique fragments (in steps 3-5) or unique molecules (step 6) originating from the docking into the two structures. As an example, there are 1205 unique fragments upon merging the two sets of 1000 fragments (one set for each Thr693 orientation) with most favourable binding energy calculated by SEED.
[b] Most interesting set (mis): flexible-ligand docking using the three fragments with the highest chemical richness (sum over the entries in the DAIM molecular fingerprint) as anchors.
[c] Maximum diversity set (mds): flexible-ligand docking using the three fragments which are most dissimilar to each other as anchors. The compounds docked using "mds" are a subset of the compounds using "mis".

EphB4 model. Since the crystal structure of the kinase domain of EphB4 is not known, a homology model was built using the structure of EphB2 (mouse, PDB entry 1JPA) as template. The overall amino acid sequence identity between the human EphB4 sequence obtained from SWISS-PROT (accession code P54760) and the sequence derived from the mouse EphB2 structure is 88.4% and there are no gaps or insertions in the aligned region. An additionally generated binary sequence alignment with the sequence derived from the human Eph kinase structure EphA2 (PDB entry 1MQB) revealed a lower sequence identity of 63.1% and also three short regions containing gaps or insertions. Therefore, only the sequence alignment between EphB4 (human) and EphB2 (mouse) was used in the initial phase of the homology modelling procedure. All sequence alignments were performed using the program Clustal W (Thompson J. D. et al., Nucleic Acids Res 1994, 22:4673-4680). The 1JPA crystal structure comprises two chemically identical subunits in the crystallographic asymmetric unit. A structural superposition of the two subunits results in an average root-mean square deviation of 0.32 Å for 269 $C_\alpha$ atoms. Since subunit A of the 1JPA crystal structure has better main-chain dihedral angles ($\phi$ and $\psi$) and lower B factors, this subunit was initially chosen as the template structure. However, the two subunits of the 1JPA structure show some clear structural differences around the active site region. The differing amino acid residues were analyzed with respect to B factors, possible contacts and stereochemical criteria. Subsequently, the side-chain rotamer conformations of the initial template structure (subunit A) were replaced by the corresponding side-chain conformations of subunit B of the 1JPA crystal structure, if the latter were better defined according to the above-mentioned criteria. The resulting modified structure was then used as template for homology modelling and a total of 100 different models were generated using the program Modeller.

The obtained initial models were ranked and analyzed based on internal energy and stereochemical sensibility. The best model was manually modified by comparison with the active sites of the two known Eph kinase structures (PDB entry codes 1JPA and 1MQB) and other related kinase structures (PDB entry codes 1BYG, 1FMK, 1FPU, 1IEP, 1M14, 1M17, 1M52, 1MP8, 1OPK, 1OPL and 2SRC) found by PSI-BLAST and DALI searches of protein structure databases. The conformational information contained in these homologous structures was used for manually adjusting side-chain conformations of conserved or similar amino acid residues. For some of the mutated residues statistically preferred X-angles were chosen and favourable hydrophobic or polar contacts were also considered. Additionally, an ATP molecule was modelled into the active site to avoid structural changes during minimization.

Minimization and ranking. After docking, multiple poses of each compound were minimized and filtered according to thresholds in van der Waals energy and van der Waals efficiency (the ratio of the van der Waals energy and the molecular weight). A general linear interaction energy with continuum electrostatics (LIECE, Huang D. and Caflisch A., J Med Chem 2004, 47:5791-5797) model was used for the final ranking.

LIECE model for kinases. The LIECE model was developed using a composite set of 165 known inhibitors, i.e., 73, 51, and 41 inhibitors of cyclin-dependent kinase 2 (CDK2), lymphocyte-specific kinase (Lck), and p38 mitogen-activated protein kinase (p38), respectively. It showed a very low root-mean-square of the error (rmse) of only 1.03 kcal·mol$^{-1}$ for the 165 inhibitors used as training set in the fitting and a leave-one-out cross-validated $q^2$ of 0.74. This model was also cross-validated on a set of compounds not used for fitting, namely 128 known inhibitors of the epidermal growth factor receptor (EGFR) tyrosine kinase. On this set, the model yielded an rmse of 1.46 kcal·mol$^{-1}$.

Library tailoring by ALTA using the EphB4 structure. Only fragments involved in two or more hydrogen bonds with the EphB4 hinge region were considered in ALTA. Fragments were ranked according to binding energy calculated by SEED (which includes continuum electrostatics solvation). The union of the two sets of 1000 fragments (one set for each protein structure differing in the orientation of the hydroxy group of Thr693) with the most favourable calculated binding energy consists of 1,205 unique fragments. A subset of 21,418 compounds was retrieved from the composite library of 728,202 molecules (step 5 in Scheme 1) using these 1,205 fragments.

In vitro validation. 40 compounds from the high-throughput docking of the focused library of 21,418 molecules were selected upon ranking (step 6 in Scheme 1) and tested first in a fluorescence resonance energy transfer (FRET)-based enzymatic assay. 10 of these could not be measured, because they interfered with the fluorescence read-out. Compound 9 with a phenylurea anchor showed an $IC_{50}$ of 76 µM in the FRET-based enzymatic assay. In the same assay, compound 2 with a three-ring system as anchor (Table 2) showed an $IC_{50}$ of about 1.6 µM, with a molecular weight of only 353 Da. Table 2 shows also the values for the related compounds 3-8 with the same basic structure according to the invention. Five more compounds with different anchors inhibited the activity of EphB4 by 15-40% at a concentration of 125 µM.

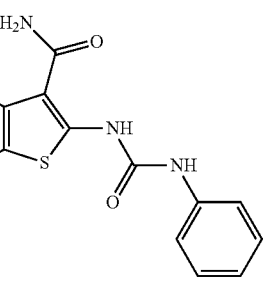

9

The ligand efficiency ($LE=-\Delta G^{exp}_{binding}$/HAC, where HAC is the number of heavy atoms) is a useful measure for lead selection. Notably, inhibitor 2 has an LE value of 0.3 kcal·mol$^{-1}$ per heavy atom suggesting that it is an interesting compound for further development. To evaluate its cell permeability and cellular activity, compound 2 was tested in CHO cells for inhibition of EphB4 autophosphorylation in a mammalian cell-based environment. It shows only mild inhibitory effects in CHO cells at a concentration of 20 µM. To further investigate cellular activity and determine whether lack thereof is a general problem of this class of molecules, further molecules containing the scaffold of compound 2 were analysed. Compounds 3 and 4 show low-micromolar inhibitory activity in the enzymatic assay (Z'Lyte). Compounds 5, 6, 7 and 8 display activity in the mid-micromolar range, with similar activities when tested in CHO cells. The similar potency of inhibitors 2-8 is consistent with the binding mode obtained by docking in which the flexible tail (substituent $R^3$) is not involved in direct interactions with atoms in the ATP-binding site.

The compounds showing the strongest inhibition effects in the enzymatic assay (2 and 3) were verified in a FRET-based enzymatic assay offered by Cerep (France). Similar values of $IC_{50}$ compared to the original FRET-based enzymatic assay (Z'Lyte) are obtained (Table 2).

As a representative of the entire series, inhibitor 2 was investigated further to provide evidence against unspecific binding due to compound aggregation. The Omnia kinetic assay was performed under two conditions, with and without the addition of detergent (0.01% Triton X-100). The $IC_{50}$ values of inhibitor 2 in the two experiments are 5.6 and 7.9 µM, which corresponds to a $K_i$ of 2.7 and 2.9 µM, respectively (FIG. 1). Such detergent-insensitive inhibition is indicative of specific binding.

TABLE 2

EphB4 inhibitors 2-8

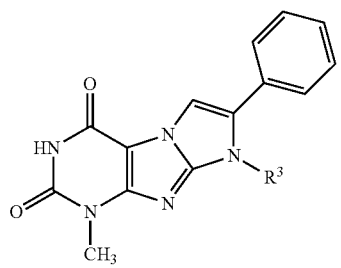

2-8

| | Structure | MW | Enzymatic assays $IC_{50}$ [µM] | | | Cell-based | Predicted $\Delta G^f$ |
|---|---|---|---|---|---|---|---|
| Cpd. | $R^3 =$ | [Da] | Z'Lyte[a] | Cerep[b] | Omnia[c] | assay[d] [%][e] | [kcal · mol$^{-1}$] |
| 2 | —(CH$_2$)$_4$OH | 353 | 1.4, 1.8 | 6.8 | 5.6, 7.9 | neg. | −11.0 |
| 3 | —(CH$_2$)$_3$CH$_3$ | 337 | 1.5, 1.5 | 8.3 | n.d. | neg. | −10.7 |
| 4 | —(CH$_2$)$_2$CH$_3$ | 323 | 1.9 | n.d. | n.d. | neg. | |
| 5 | —o-OCH$_3$-phenyl | 387 | 27 | n.d. | n.d. | 14% at 20 µM | |
| 6 | —(CH$_2$)$_3$OCH$_3$ | 353 | 50 | n.d. | n.d. | 28% at 20 µM | |
| 7 | —(CH$_2$)$_2$-phenyl | 385 | 30% at 14 µM[e] | n.d. | n.d. | 34% at 20 µM | |
| 8 | —(CH$_2$)$_2$—m-CH$_2$-phenyl | 399 | 29% at 5 µM[e] | n.d. | n.d. | 14% at 20 µM | |

[a]Z'Lyte FRET-based enzymatic assay
[b]Cerep FRET-based enzymatic assay
[c]Omnia kinetic assay
[d]in CHO cells
[e]Percent inhibition at specified concentration
[f]Free energy of binding calculated by LIECE To further analyze the competitive behaviour of inhibitor 2, different ATP concentrations are used in the Omnia kinetic assay (ranging from 31.25 to 500 µM). The data obtained in these experiments are shown in a specific velocity plot (FIG. 2), where the ratio of the initial velocities for the non-inhibited and inhibited reactions at a given ATP concentration ($v_0/v_i$ in FIG. 2) is plotted versus $\sigma/(1+\sigma)$, with $\sigma=[ATP]/K_m$. For an ATP competitive inhibitor, all curves should intersect close to the point (1,1), which is the case for inhibitor 2. This result provides strong evidence that inhibitor 2 does indeed bind to the ATP binding site, as predicted by the docking calculations.

Improving the lead inhibitor, compound 2. For the compounds of the present invention of formula 1, the potency is improved by improving the hydrogen bond network with the receptor. A substituent $R^1$ other than hydrogen is introduced (hydroxy, sulfhydryl, amino or lower alkylamino), which improves the binding by a hydrogen bond with C=O of Glu694 and the OH of Thr693. A substituent $R^2$ other than methyl containing e.g. sulfonyl oxygen or carbonyl oxygen able to interact with the NH of Ala700 further improves binding. Since compounds of type 2 have a low $K_d$ in organic solvents, other substituents $R^3$ may improve and/or adjust the solubility of the compounds of the invention without substantially disturbing the docketing properties. Substituents $R^4$ and $R^5$ of the phenyl ring may improve the properties in the apolar pocket, however, are severely restricted in size.

TABLE 3

$IC_{50}$ and % inhibition

| Compound No. | | Formula | MW | $IC_{50}$ (µM) | % inhibition at indicated concentration C |
|---|---|---|---|---|---|
| 2 | STOCK 3S-89331 | | 353 | 8; 7; 6.7; 7 | C = 10 µM: 72; 67; 68; 59; 64 |
| 3 | STOCK 3S-87561 | | 337 | 1.9; 2 | C = 10 µM: 89; 82; 99 |
| 4 | STOCK 3S-86417 | | 332 | 8; 9 | C = 10 µM: 62; 58; 54 |
| 5 | STOCK 5S-32458 | | 387 | 3.5, 5.3, 3.3, 1.5 | C = 10 µM: 75; 84; 74; 71; 80 |

TABLE 3-continued

IC$_{50}$ and % inhibition

| Compound No. | Formula | MW | IC$_{50}$ (μM) | % inhibition at indicated concentration C |
|---|---|---|---|---|
| 6 STOCK 5S-39703 | | 353 | | C = 10 μM: 49; 46; 46 |
| 15 STOCK 6S-12314 | | 339 | | C = 10 μM: 11; 50; 1 |
| 16 STOCK 6S-32353 | | 435 | | C = 10 μM: 50; 28 |
| 17 STOCK 6S-34876 | | 435 | | C = 10 μM: 72; 62 |
| 22 LB-38 | | 481 | | C = 10 μM: 17; 1; −5 |

TABLE 3-continued
IC₅₀ and % inhibition
| Compound No. | | Formula | MW | IC₅₀ (μM) | % inhibition at indicated concentration C |
|---|---|---|---|---|---|
| 23 | LB-45 | 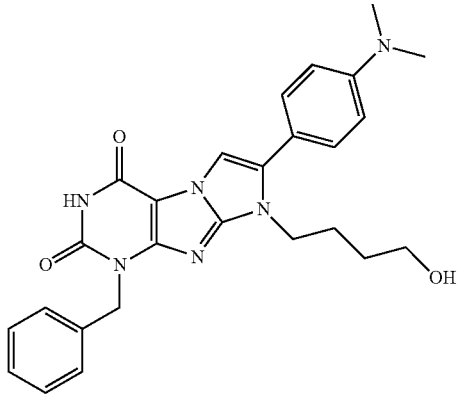 [SMILES: CN(C)c1ccc(-c2cn3c4c(=O)[nH]c(=O)n(Cc5ccccc5)c4nc3n2CCCCO)cc1] | 472 | | C = 10 μM: 33; 7 |
| 24 | LB-47 | 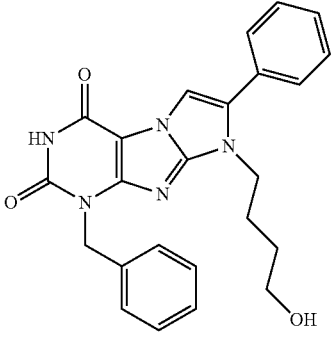 [SMILES: O=c1[nH]c(=O)n(Cc2ccccc2)c2nc3n(CCCCO)c(-c4ccccc4)cn3c12] | 429 | | C = 10 μM: 7; −4 C = 30 μM: 0; 15 |
| 25 | LB-50 | 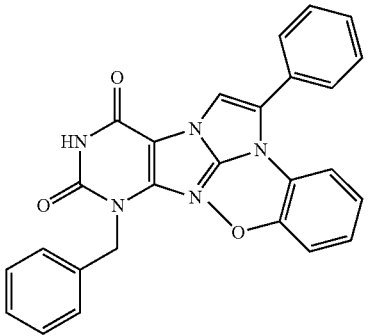 [SMILES: COc1ccccc1-n1c(-c2ccccc2)cn2c3c(=O)[nH]c(=O)n(Cc4ccccc4)c3nc12] | 463 | | C = 10 μM: 15; 11 C = 30 μM: 17; 1 |
| 26 | LA-51 | 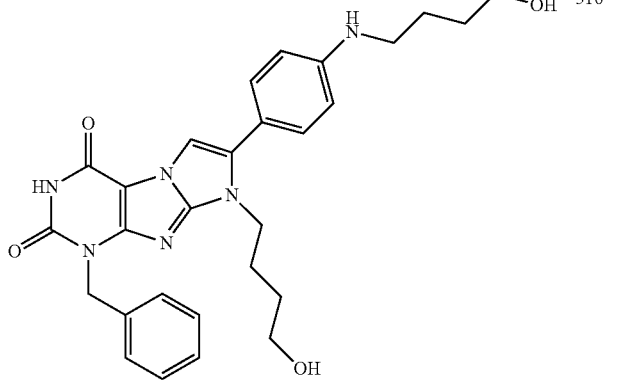 | 516 | | C = 20 μM: 42; 20 |

TABLE 3-continued
IC$_{50}$ and % inhibition
| Compound No. | | Formula | MW | IC$_{50}$ (μM) | % inhibition at indicated concentration C |
|---|---|---|---|---|---|
| 28 | LC-60 | 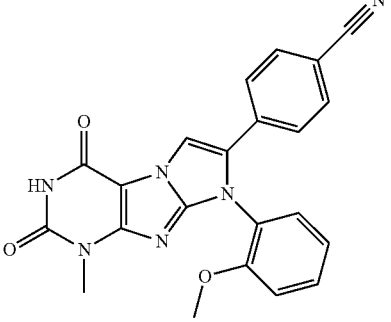 | 412 | | C = 20 μM: 13; 17 |
| 29 | LC-66 | 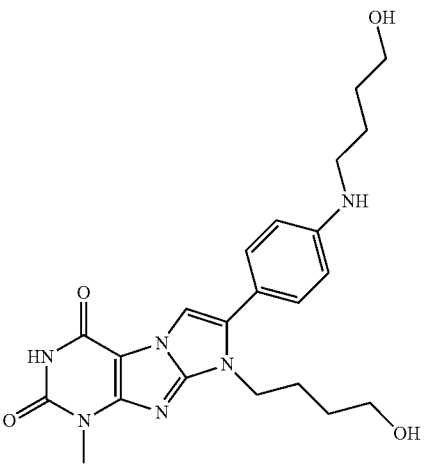 [SMILES: Cn1c(=O)[nH]c(=O)c2c1nc1n(CCCCO)c(-c3ccc(NCCCCO)cc3)cn21] | 440 | | C = 20 μM: 50; 62; 37; 34 |
| 30 | LB-60 | 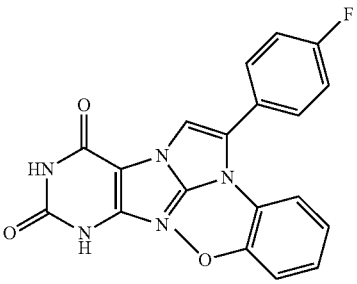 [SMILES: COc1ccccc1-n1c(-c2ccc(F)cc2)cn2c3c(=O)[nH]c(=O)[nH]c3nc12] | 391 | 4.6; 6.2 | |
| 32 | LB-91 | 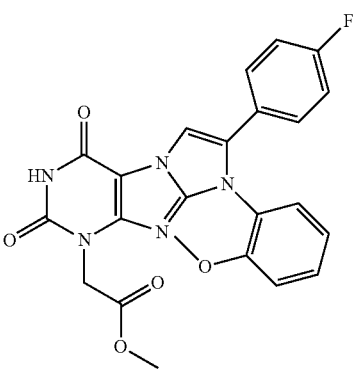 [SMILES: COC(=O)Cn1c(=O)[nH]c(=O)c2c1nc1n(-c3ccccc3OC)c(-c3ccc(F)cc3)cn21] | 463 | 9.5; 8.9 | |

TABLE 3-continued
| | | | | % inhibition at indicated |
|---|---|---|---|---|
| Compound No. | Formula | MW | IC$_{50}$ (μM) | concentration C |
| 34 LB-103 | 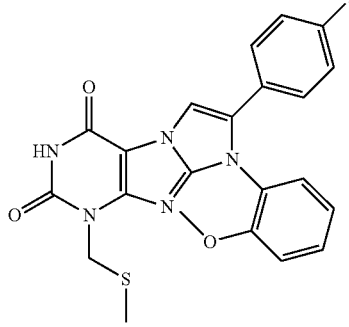 | 451 | 5.1; 6.4 | |
| 35 LB-104 | 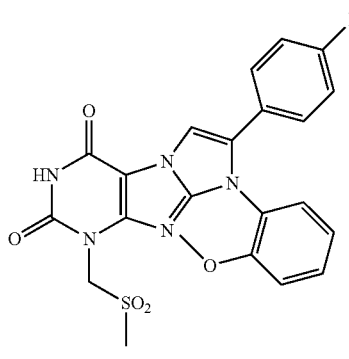 | 483 | 7.9; 7.1 | |
| 36 LB-32 | 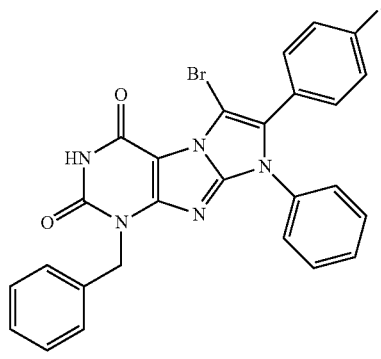 | 530 | | C = 10 μM: 10; 10; 4 |
| 40 LC-54 | 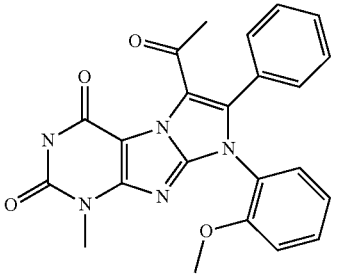 [SMILES: COc1ccccc1-n1c(-c2ccccc2)c(C(C)=O)n2c3c(=O)[nH]c(=O)n(C)c3nc12] | 429 | | C = 20 μM: 14; 20 |

TABLE 3-continued

IC$_{50}$ and % inhibition

| Compound No. | | Formula | MW | IC$_{50}$ (μM) | % inhibition at indicated concentration C |
|---|---|---|---|---|---|
| 41 | LC-55 | | 412 | | C = 20 μM: 21; 30 |
| 44 | LC-69 | | 431 | | C = 20 μM: 12; 23; 19; 13 |
| 45 | LC-80 | | 382 | | C = 20 μM: 8; 9; 14; 16 |

Synthesis of compounds of the invention. Compounds of formula 1, wherein $R^1$ is hydrogen, are available by reaction of the potassium salt of 3-substituted 8-chloro-xanthines 10 with optionally substituted phenacyl halides 11 to give intermediate 12 which is cyclised by reaction with a primary amine $R^3$—NH$_2$.

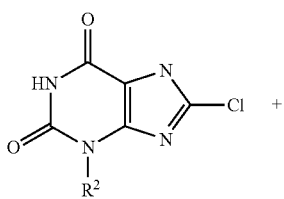

10

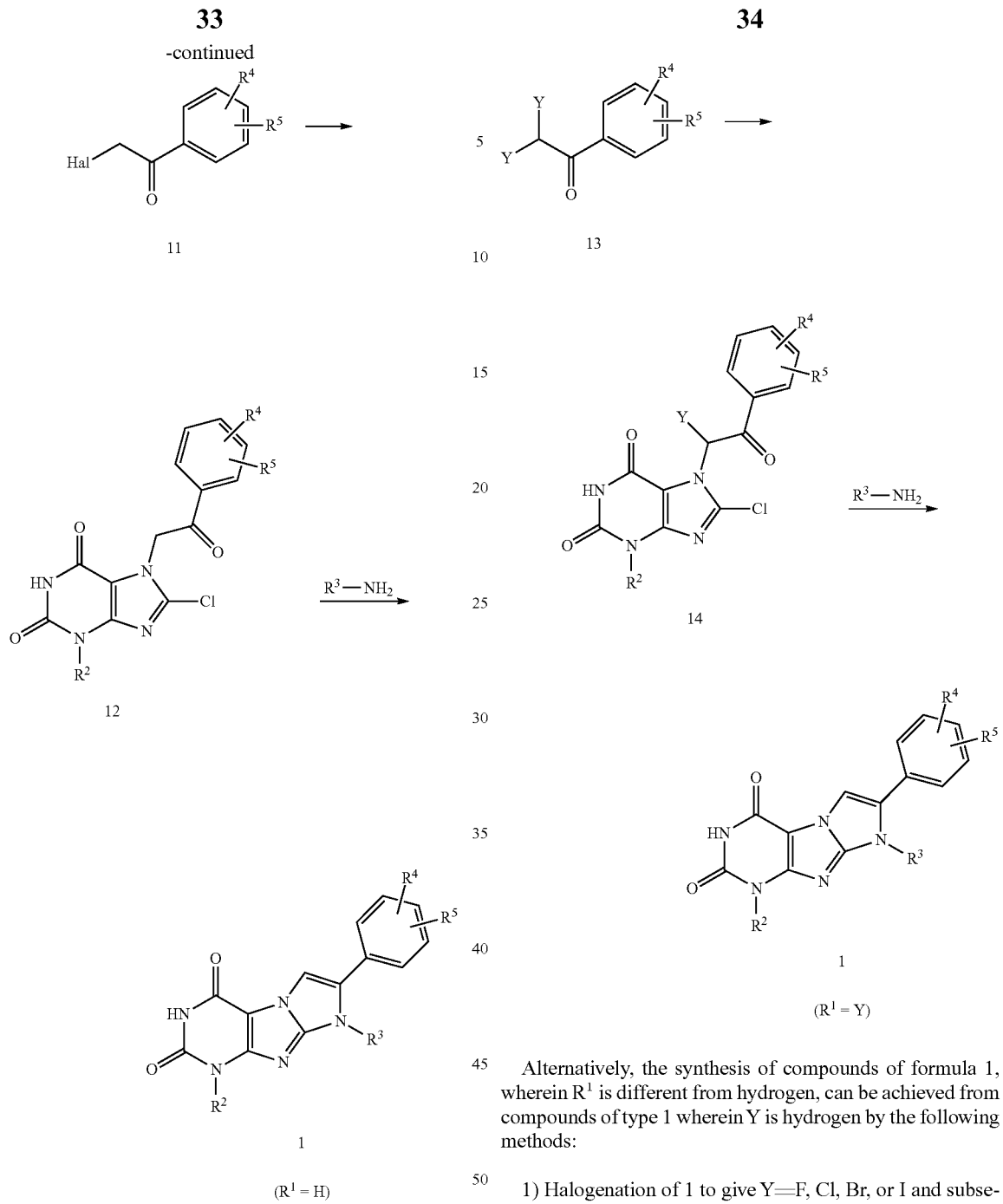

For the synthesis of compounds of formula 1, wherein $R^1$ is different from hydrogen, the corresponding optionally substituted phenacyl halide 11 is replaced by a doubly functionalized phenacyl derivative 13 wherein Y represents $R^1$, a protected version of $R^1$ or a precursor of $R^1$, for example chlorine, bromine, iodine or triflate. On reaction of the corresponding intermediate 14 with primary amine $R^3$—$NH_2$, a compound of formula 1 is formed wherein substituent Y still has to be converted to $R^1$, which may be accomplished by palladium catalyzed cross-coupling reaction transferring Y into hydroxy or amino.

Alternatively, the synthesis of compounds of formula 1, wherein $R^1$ is different from hydrogen, can be achieved from compounds of type 1 wherein Y is hydrogen by the following methods:

1) Halogenation of 1 to give Y=F, Cl, Br, or I and subsequent substitution reaction with a nucleophile such as CuCN or $NaN_3$ to give Y=CN or $N_3$, respectively. The corresponding compounds obtained by this method can be further derivatized to the corresponding carboxylic acid, esters, amides, thioamides, aminomethyl compounds, and amines, and related compounds. In addition, compounds of type 1 (Y=F, Cl, Br, I) can be used as starting materials for a palladium-catalyzed cross-coupling reaction, wherein Y is transformed into amino, hydroxy and alkyl-, aryl or heteroarylcarbonyl.

2) Electrophilic substitution of 1 with electrophiles such as nitronium or acyl cation to give Y=$NO_2$ and $COCH_3$, respectively, and subsequent modification of these groups to obtain derivatives in which Y is amino, alkylcarbonyloxy and hydroxy.

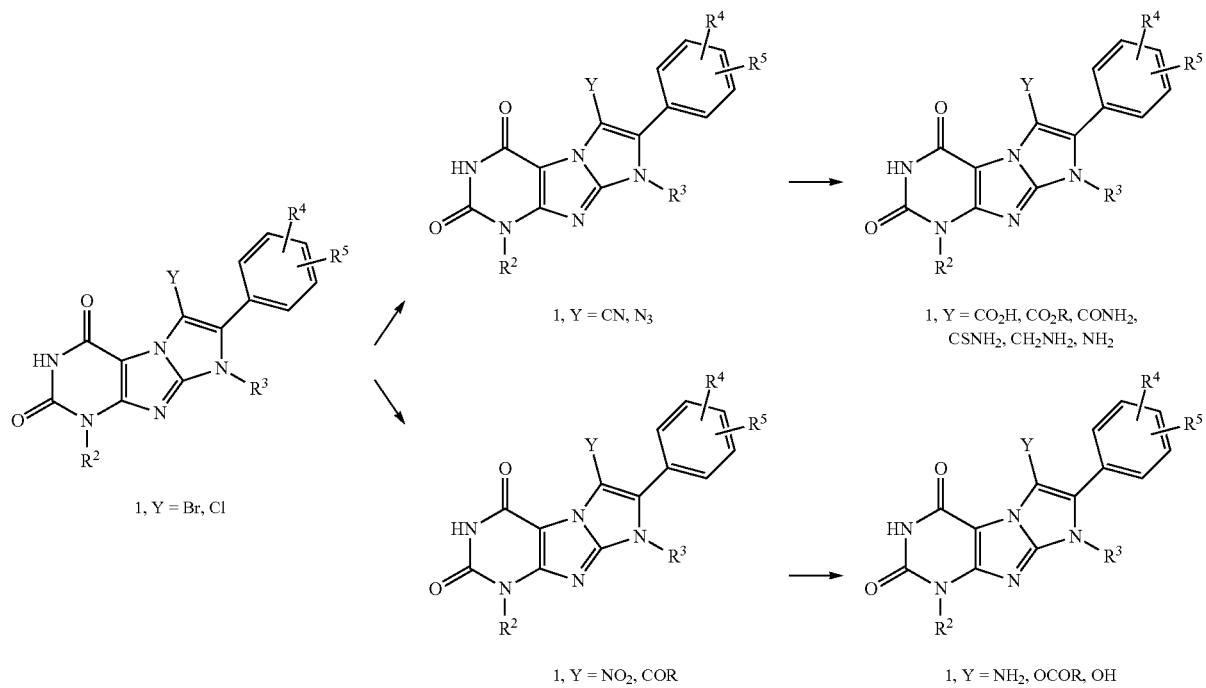
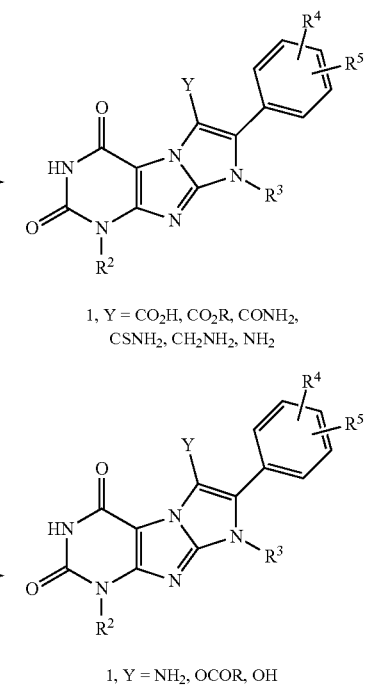

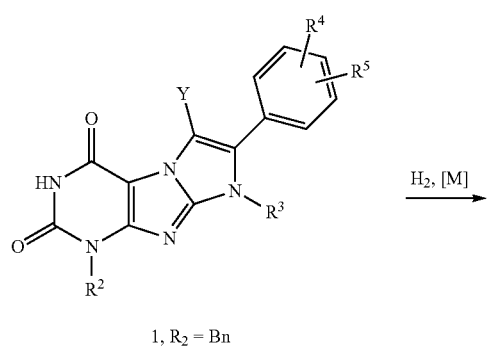

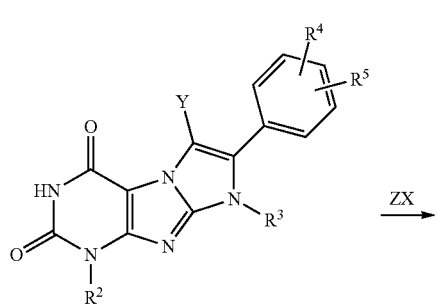

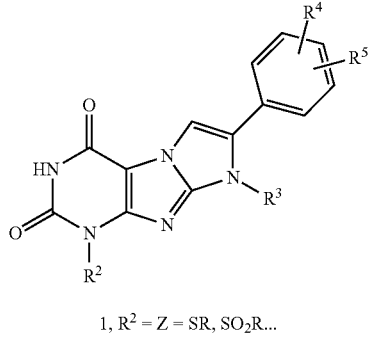

Finally, the synthesis of compounds wherein $R^2$ is lower alkyl, arylsulfonyl, heteroarylsulfonyl, lower alkylsulfonyl, arylcarbonyl, heteroarylcarbonyl, lower alkylcarbonyl, lower alkoxycarbonyl, aminocarbonyl, carboxy, and the like is accomplished from compound 1 wherein $R^2$ is a protecting group (such as benzyl) which can be removed by hydrogenation and subsequent alkylation at N2 with the corresponding alkylating agents.

Xanthines of type 10 are readily available by standard condensation reactions of malonitriles with $R^2$-substituted ureas in the presence of a strong base followed by amination, formylation and subsequent cyclization, then chlorination at $C^8$ in hydrochloric/acetic acid and deprotonation at $N^7$ with potassium carbonate.

Computational requirements. It is interesting to compare the CPU time required for the preparation and docking of the focused library with docking of all compounds in the three libraries. The ALTA approach required about 6500 hours (on a Linux cluster with CPUs with clock speeds of 1.7 GHz): 2 hours for decomposition into fragments, 2,200 hours for fragment docking, 1,000 hours for substructure search, and 3,300 hours for flexible-ligand docking and energy minimization. The focused library contains $1/34^{th}$ of the initial collection of compounds and only about $1/3^{rd}$ of the fragments, which yields a net speed-up by a factor of about 20, a number that would be even larger in the case of flexible-protein docking. While the actual computation times per compound will naturally vary for other docking programs, the speed-up achieved by library pre-processing with the ALTA procedure will remain significant.

Figure 2:
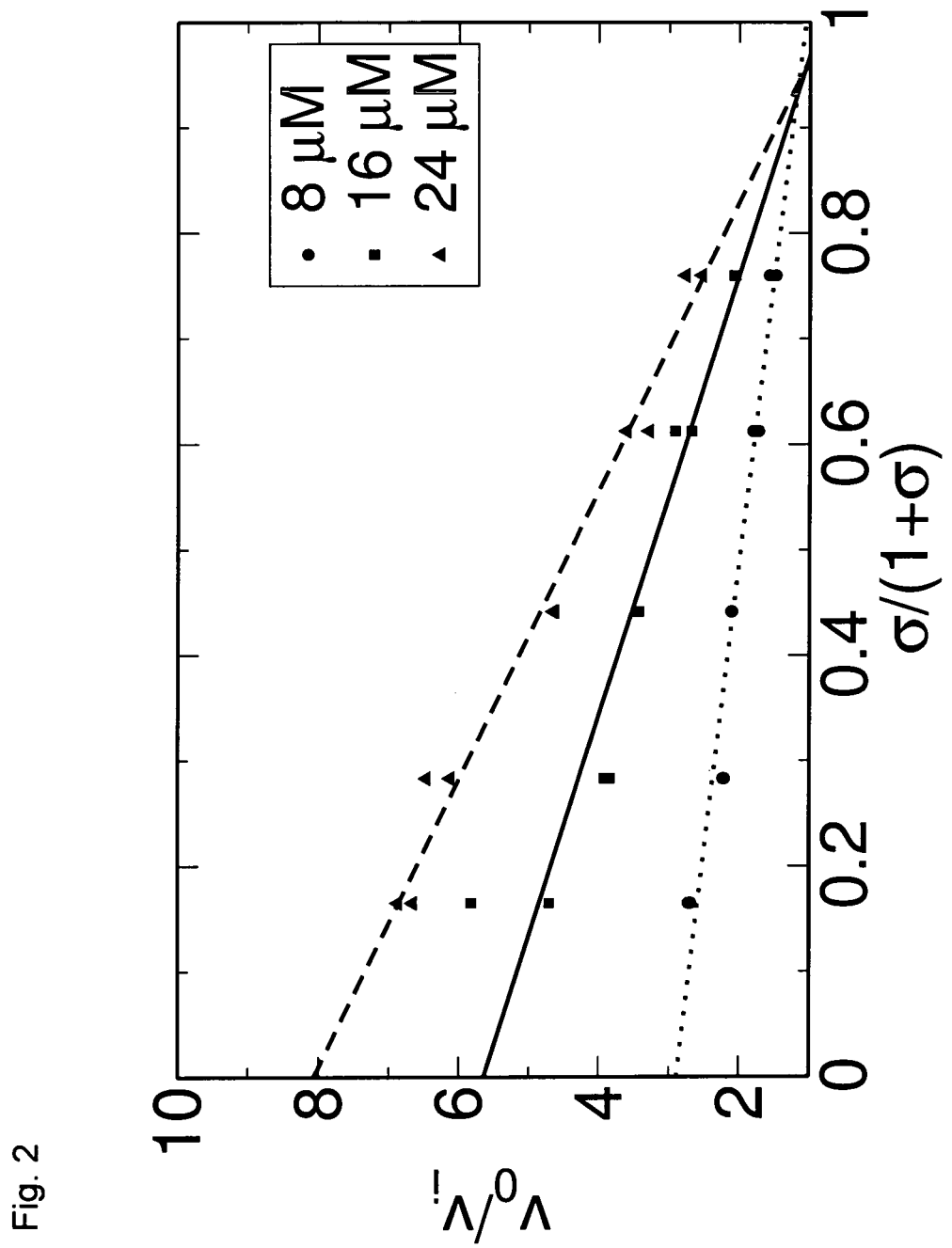
FIG. 2: Specific velocity plot for compound 2. $v_0/v_i$ is the ratio of the initial velocities for the non-inhibited and inhibited reactions at a given ATP concentration. All values were measured in duplicates, but some of the pairs of data points almost completely overlap on the plot. σ is the ratio of the ATP concentration and its $K_m$, which was 158 µM in this experiment. ATP concentrations ranged from 31.25 to 500 µM. Intersecting of all curves close to (1,1) indicates that compound 2 is ATP competitive. Measurements were carried out by the Omnia kinetic assay described hereinbelow.
Figure 3:
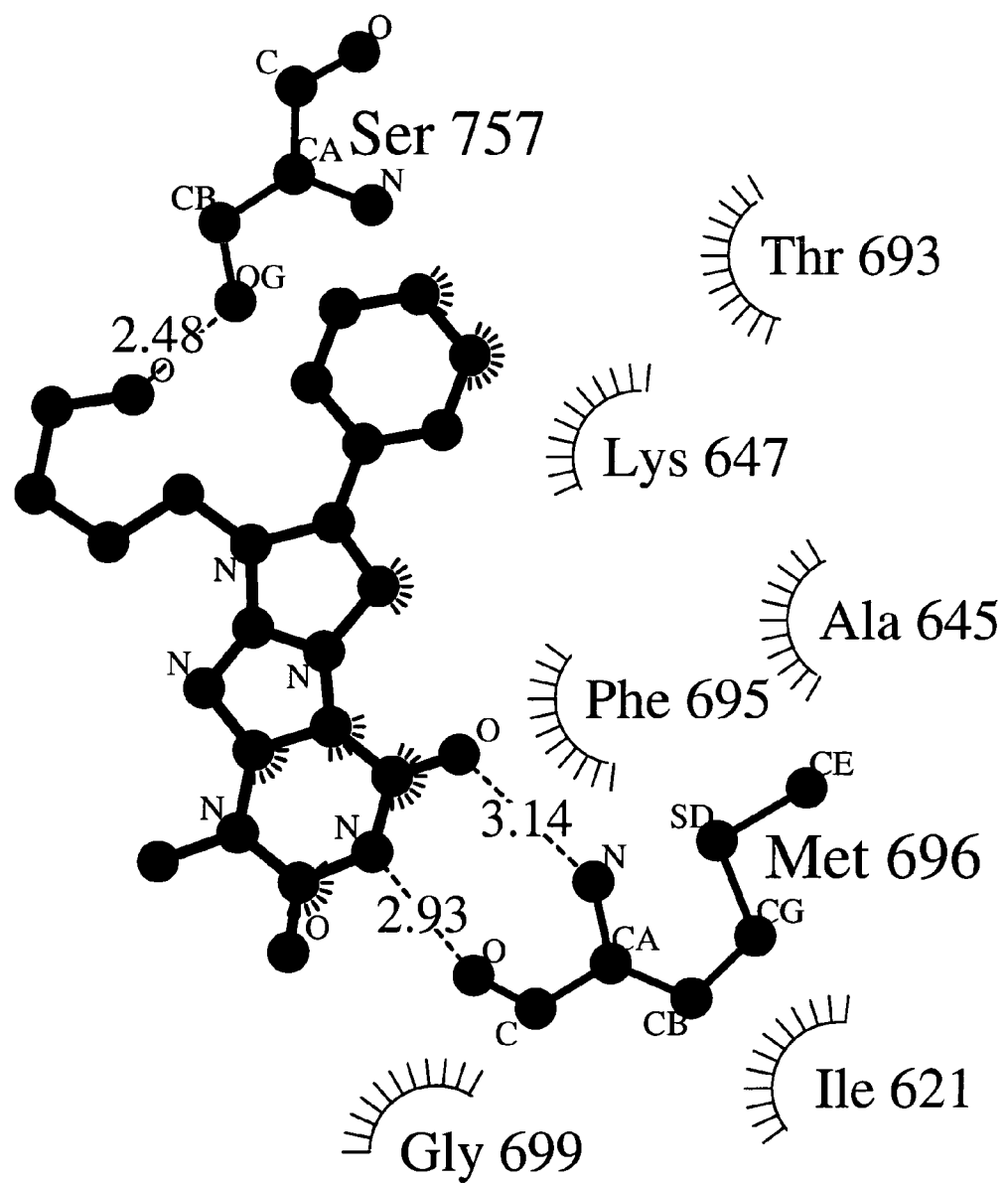
FIG. 3: Calculated binding mode of compound 2. Compound 2 and Ser757 and Met696 are shown as stick and ball models. Dashed lines are hydrogen bonds with bond length in Å. Hydrophobic interactions are shown as semi-circles with hatched lines.

Kinetic assay. Compound 2 was tested in the Omnia Tyr Recombinant Kit KNZ4051 (Biosource, USA) at different concentrations between 50 nM and 100 µM in a Corning 96-well microtiter plate. Fluorescence progress curves are measured upon excitation at 360 nm and emission at 485 nm. The assay contains a final concentration of EphB4 and ATP of 25 ng/µl and 125 µM (which is near its $K_m$), respectively, and is run at 30° C. for 1 hour. To provide evidence for specific binding, a second assay is performed in which 0.01% of Triton X-100 is added to the reaction mixture (FIG. 1). Moreover, to show the competitive behaviour of compound 2 towards ATP, different ATP concentrations (ranging from 31.25 to 500 µM) were used (FIG. 2). $IC_{50}$ values (inhibitor concentration at which enzyme activity is reduced by 50%) and fitted curves are determined with GraphPad Prism 5.0 (GraphPad Software).

Phospho-EphB4 ELISA of CHO cells. The ELISA assay was performed as follows: Chinese hamster ovary (CHO)-FRT cells are stably transfected with myc-tagged full-length human EphB4 according to the Flip-In System protocol (Invitrogen, USA). A clone that expresses myc-tagged human EphB4 and shows inducible autophosphorylation of EphB4 upon stimulation with mouse ephrinB2-Fc (mouse ephrinB2 fused to the Fc region of human IgG) is selected. Cells of this clone are preincubated with EphB4 inhibitors for 15 minutes and then stimulated with preclustered ephrinB2-Fc for 45 minutes at 37° C. Cells are lysed, transferred to a 96-well plate coated with anti-myc antibody and incubated overnight at 4° C. After incubation with anti-phosphotyrosine antibody, reactions are developed with BM Blue peroxydase substrate, and autophosphorylation of EphB4 is quantified by measuring absorption at 450 nm.

Panvera Z'Lyte. In vitro kinase activity was measured using the Panvera Z'Lyte Tyr2 kinase assay PV3191 (Invitrogen, USA), according to the manufacturer's instructions. Five dilutions of compound in a three-fold series are measured, with the highest concentration being 125 µM. The reaction assay (10 µl) contains 7.5 ng of EphB4 kinase (Proqinase, Germany), 10 µM ATP, and 1% DMSO. The reaction is performed at room temperature for 1 hour. Since this assay contains Brij, a non-ionic detergent, aggregating compounds (i.e., promiscuous binders) should not show inhibition.

Cerep. The assays performed at Cerep (Celle l'Evescault, France) were done in duplicates at eight different concentrations ranging from 10 nM to 20 µM. The concentration of ATP is 0.75 µM in the assays for EphB4 at a concentration of 0.2 µg/ml.

Biosource Omnia. To provide more evidence against unspecific binding, compound 9 was tested in the Omnia Tyr Recombinant Kit KNZ4051 (Biosource, USA) twice, i.e., without detergent and with 0.01% Triton X-100. In each of the two experiments, the compound is measured in duplicates at eight different concentrations between 50 nM and 100 µM. EphB4 kinase (Proqinase, Germany) and ATP are used at final concentrations of 25 ng/µl and 125 µM, respectively. The assay is run at 30° C. for 1 hour.

EXAMPLES

All reactions were carried out under a nitrogen atmosphere using Standard Schlenk-lines. All reagents were used as received unless otherwise noted. Solvents were purchased in the best quality available, degassed by purging thoroughly with nitrogen and dried over activated molecular sieves of appropriate size. Alternatively, they were purged with argon and passed through alumina columns in a solvent purification system (Innovative Technology). Reactions were monitored by thin layer chromatography (TLC) using Merck TLC silica gel 60 $F_{254}$. Flash column chromatography was performed over silica gel (230-400 mesh). NMR spectra were recorded on AV2 400 or AV2 500 MHz Bruker spectrometers. Chemical shifts are given in ppm. The spectra are calibrated to the residual $^1H$ and $^{13}C$ signals of the solvents. Multiplicities are abbreviated as follows: singlet (s), doublet (d), triplet (t), quartet (q), doublet-doublet (dd), quintet (quint), sextuplet (sext), septet (sept), multiplet (m), and broad (br). High-resolution electrospray ionization mass spectrometry was performed on a Finnigan MAT 900 (Thermo Finnigan, San Jose, Calif.; USA) doublefocusing magnetic sector mass spectrometer. Ten spectra were acquired. A mass accuracy ≤2 ppm was obtained in the peak matching acquisition mode by using a solution containing 2 µl PEG200, 2 µl PPG450, and 1.5 mg NaOAc (all obtained from Sigma-Aldrich, CH-Buchs) dissolved in 100 ml MeOH (HPLC Supra grade, Scharlau, E-Barcelona) as internal standard. LC-MS analysis was done on a Finnigan Voyager GC8000 Top.

General Procedure for the Cyclization of alkylated xanthines

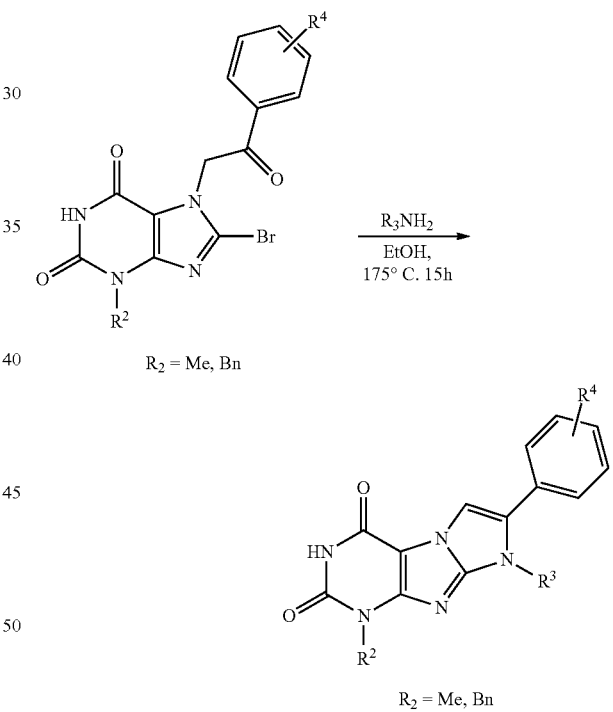

A mixture of 3-alkyl-8-bromo-3,7-dihydro-7-(2-oxo-2-phenyl-ethyl)-1H-purine-2,6-dione (Priymenko, B. A.; Samura, B. A.; Garmash, S. N.; Klyuev, N. A.; Romanenko, N. I. Pharmaceutical Chemistry Journal 1983, 17, 105-108) (1.0 equiv) and the corresponding primary amine (4.0 equiv) in EtOH (concentration, 0.1 M) was heated in a sealed tube at 175° C. for 12 h. The reaction was cooled to room temperature, the solid was filtered off, and washed with water affording the corresponding products in pure form. This method was used to obtain: LA-93 (18), LA-95 (19), LA-103 (20), LB-24-3 (21), LB-38 (22), LB-45 (23), LB-47 (24), LB-50 (25), LA-51 (26), LC-57(27), LC-60 (28), LC-66 (29).

1-Benzyl-7-phenyl-1H-imidazo[2,1-f]purine-2,4(3H,9H)-dione (18, LA-93)

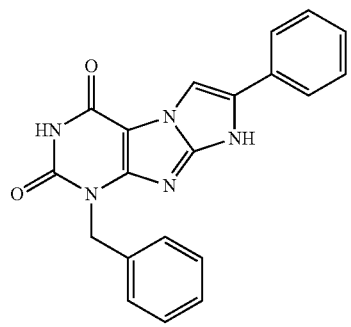

Yield: 33%; mp 393-395° C.; $^1$H NMR (400 MHz, DMSO-$d_6$): δ=10.99 (s, 1H), 8.12 (s, 1H), 7.79 (d, J=7.6 Hz, 2H), 7.26-7.46 (m, 8H), 5.14 (s, 2H), N$_3$H—not observed; $^{13}$C NMR (100 MHz, DMSO-$d_6$): δ=153.1, 152.7, 150.8, 148.2, 137.1, 130.7, 128.9, 128.8, 128.2, 127.8, 127.4, 127.1, 124.3, 103.8, 98.5, 45.0; IR (film): ν=3145, 3030, 2823, 1705, 1667, 1451, 1257, 1159, 721, 589 cm−1; MS (ESI): m/z: calcd for $C_{20}H_{15}N_5O_2Na^+$: 380.3, found: 380.1.

1-Benzyl-8-methyl-7-phenyl-1H-imidazo[2,1-f]purine-2,4(3H,8H)-dione (19, LA-95)

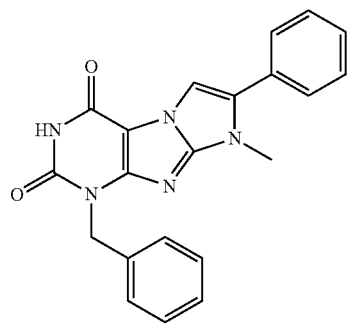

Yield: 22%; mp 306-308° C.; $^1$H NMR (400 MHz, DMSO-$d_6$): δ=10.51 (s, 1H), 7.78 (s, 1H), 7.63-7.65 (m, 2H), 7.47-7.55 (m, 3H), 7.24-7.37 (m, 5H), 5.17 (s, 2H), 3.68 (s, 3H); IR (film): ν=3159, 2900, 1668, 1500, 1393, 1242, 1065, 750, 536 cm$^{-1}$; MS (ESI): m/z: calcd for $C_{21}H_{17}N_5O_2Na^+$: 394.1, found: 394.2.

1-Benzyl-8-methyl-7-p-methylaminophenyl-1H-imidazo[2,1-f]purine-2,4(3H,8H)-dione (20, LA-103)

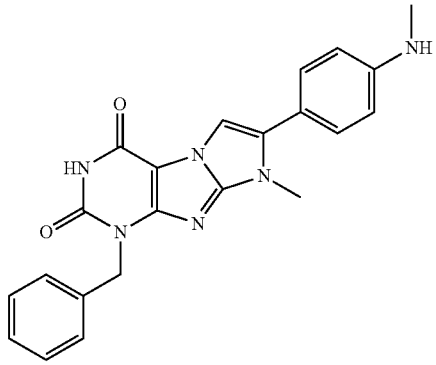

Yield: 65%; mp 288-290° C.; $^1$H NMR (400 MHz, DMSO-$d_6$): δ=10.50 (s, 1H), 7.49 (s, 1H), 7.24-7.36 (m, 7H), 6.63 (d, J=8.4 Hz, 2H), 6.03 (q, J=4.9 Hz, 1H), 5.15 (s, 2H), 3.60 (s, 3H), 2.72 (d, J=4.9 Hz, 3H); $^{13}$C NMR (100 MHz, DMSO-$d_6$): δ=153.2, 152.0, 150.7, 150.3, 147.7, 137.0, 133.7, 129.6, 128.3, 127.2, 127.1, 114.0, 111.4, 102.9, 98.9, 44.9, 30.7, 29.3; IR (film): ν=3419, 3139, 3013, 2811, 1674, 1608, 1515, 1454, 1258, 1159, 701, 532 cm$^{-1}$; MS (ESI): m/z: calcd for $C_{22}H_{20}N_6O_2Na^+$: 423.4, found: 423.2.

1-Benzyl-7-p-fluorophenyl-8-phenyl-1H-imidazo[2,1-f]purine-2,4(3H,8H)-dione (21, LB-24-3)

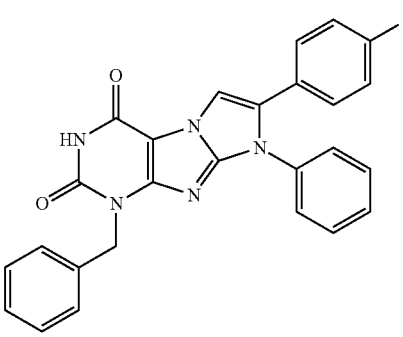

Yield: 70%; mp 250-252° C.; $^1$H NMR (400 MHz, DMSO-$d_6$): δ=11.13 (s, 1H), 8.03 (s, 1H), 7.17-7.51 (m, 14H), 5.08 (s, 2H); $^{13}$C NMR (125 MHz, DMSO-$d_6$): δ=162.0 (d, J=246.7 Hz), 153.3, 152.4, 150.6, 147.5, 136.8, 133.9, 130.8 (d, J=8.4 Hz), 129.6, 129.4, 128.5, 128.2, 127.1, 126.8, 124.2 (d, J=3.1 Hz), 123.0, 115.5 (d, J=21.8 Hz), 106.4, 99.1, 44.9; IR (film): ν=3154, 3043, 2818, 1667, 1485, 1258, 1159, 746, 533 cm$^{-1}$; MS (ESI): m/z: calcd for $C_{26}H_{18}FN_5O_2Na^+$: 474.4, found: 474.1.

1-Benzyl-7-p-fluorophenyl-8-(2-methoxyphenyl)-1H-imidazo[2,1-f]purine-2,4(3H,8H)-dione (22, LB-38)

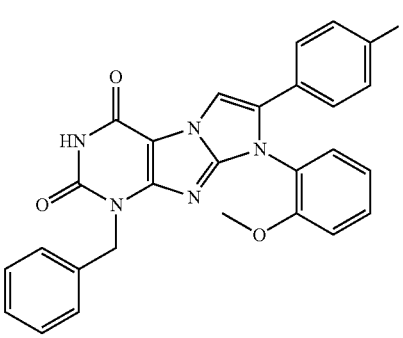

Yield: 19%; mp 251-253° C.; $^1$H NMR (500 MHz, DMSO-$d_6$): δ=11.09 (s, 1H), 7.99 (s, 1H), 7.46-7.49 (m, 2H), 7.25-7.29 (m, 6H), 7.20-7.23 (m, 1H), 7.12-7.17 (m, 3H), 7.04-7.08 (m, 1H), 5.05 (s, 2H), 3.54 (s, 3H); $^{13}$C NMR (125 MHz, DMSO-$d_6$): δ=161.9 (d, J=246.7 Hz), 154.7, 153.3, 152.4, 150.6, 147.7, 136.8, 132.0, 131.2, 129.9 (d, J=8.4 Hz), 129.6, 128.2, 127.1, 127.0, 124.6 (d, J=3.1 Hz), 122.2, 121.0, 115.4 (d, J=21.8 Hz), 113.0, 105.5, 99.1, 55.6, 44.9; IR (film):

ν=3160, 3025, 2822, 1671, 1487, 1225, 1157, 841, 744, 529, 409 cm$^{-1}$; MS (ESI): m/z: calcd for $C_{27}H_{20}FN_5O_3Na^+$: 504.4, found: 505.0.

1-Benzyl-7-p-dimethylaminophenyl-8-(4-hydroxybutyl)-1H-imidazo[2,1-f]purine-2,4(3H,8H)-dione (23, LB-45)

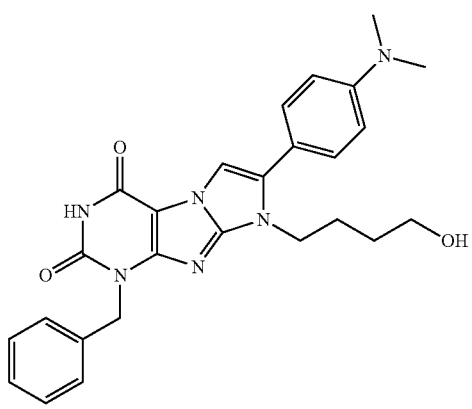

Yield: 18%; $^1$H NMR (400 MHz, DMSO-d$_6$): δ=10.97 (s, 1H), 7.50 (s, 1H), 7.24-7.40 (m, 7H), 6.82 (d, J=8.9 Hz, 2H), 5.15 (s, 2H), 4.06 (t, J=7.1 Hz, 2H), 3.26 (t, J=7.1 Hz, 2H), 2.97 (s, 6H), 1.69 (quint, J=7.1 Hz, 2H), 1.24 (quint, J=7.1 Hz, 2H), OH—not observed; $^{13}$C NMR (100 MHz, DMSO-d$_6$): δ=154.2, 153.1, 151.7, 151.5, 148.6, 138.1, 134.1, 130.8, 129.3, 128.6, 128.2, 115.7, 113.0, 104.8, 99.9, 60.9, 46.0, 44.5, 30.1 (2C), 26.0; IR (film): ν=3374, 3036, 2814, 1689, 1605, 1514, 1445, 1257, 1192, 743, 586 cm$^{-1}$; MS (ESI): m/z: calcd for $C_{26}H_{28}N_6O_3Na^+$: 495.5, found: 495.2.

1-Benzyl-8-(4-hydroxybutyl)-7-phenyl-1H-imidazo[2,1-f]purine-2,4(3H,8H)-dione (24, LB-47)

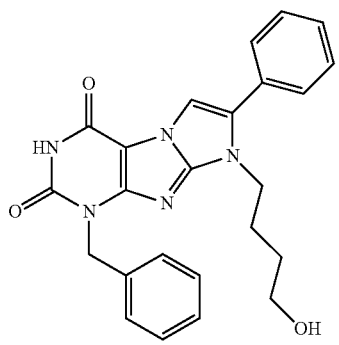

Yield: 28%; $^1$H NMR (500 MHz, DMSO-d$_6$): δ=11.01 (s, 1H), 7.72 (s, 1H), 7.59 (d, J=7.4 Hz, 2H), 7.48-7.55 (m, 3H), 7.39 (d, J=7.4 Hz, 2H), 7.30-7.33 (m, 2H), 7.25-7.28 (m, 1H), 5.15 (s, 2H), 4.11 (t, J=7.4 Hz, 2H), 3.38 (m, 1H), 3.24 (t, J=7.4 Hz, 2H), 1.67 (quint, J=7.4 Hz, 2H), 1.22 (m, 2H); IR (film): ν=3369, 3044, 2864, 1661, 1498, 1450, 1042, 692 cm$^{-1}$; MS (ESI): m/z: calcd for $C_{24}H_{23}N_5O_3Na^+$: 452.4, found: 452.2.

1-Benzyl-8-(2-methoxyphenyl)-7-phenyl-1H-imidazo[2,1-f]purine-2,4(3H,8H)-dione (25, LB-50)

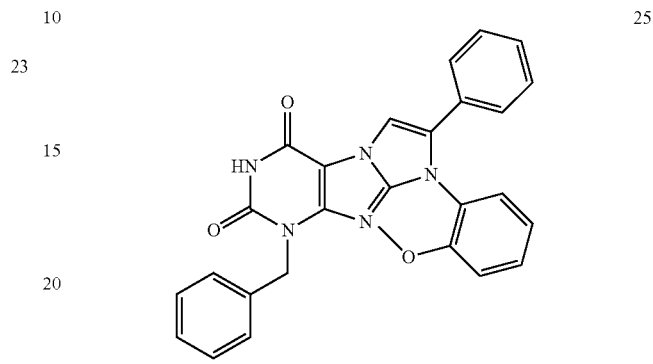

Yield: 40%; mp 301-303° C.; $^1$H NMR (400 MHz, DMSO-d$_6$): δ=11.08 (s, 1H), 8.00 (s, 1H), 7.46-7.50 (m, 2H), 7.23-7.29 (m, 10H), 7.18 (d, J=7.8 Hz, 1H), 7.06 (t, J=7.8 Hz, 1H), 5.06 (s, 2H), 3.54 (s, 3H); $^{13}$C NMR (100 MHz, DMSO-d$_6$, CDCl$_3$): δ=154.7, 153.3, 152.4, 150.6, 147.8, 136.8, 132.9, 131.1, 129.5, 128.3, 128.2, 128.0, 127.5, 127.1, 127.0, 122.4, 120.9, 113.0, 105.4, 99.1, 55.6, 44.9, 1C missing due to overlapping; IR (film): ν=3151, 3030, 2817, 1669, 1488, 1263, 1155, 1024, 754, 529 cm$^{-1}$; HRMS (ESI): m/z: calcd for $C_{27}H_{21}N_5O_3Na^+$: 486.1542, found: 486.1540.

1-Benzyl-8-(4-hydroxybutyl)-7-p-(4-hydroxybutyl)-phenyl-1H-imidazo[2,1-f]purine-2,4(3H,8H)-dione (26, LA-51)

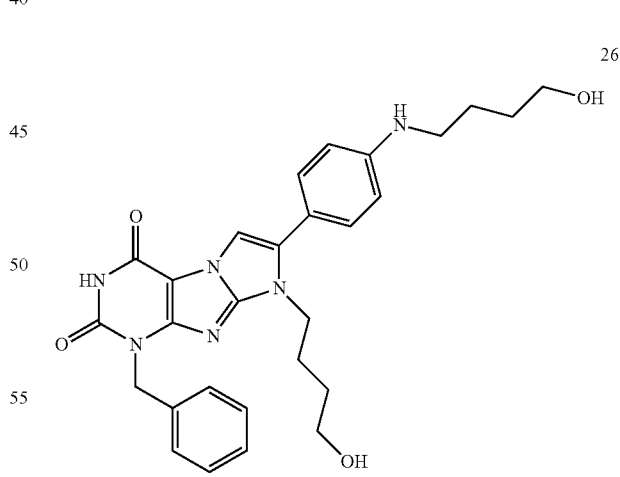

Yield: 32%; $^1$H NMR (500 MHz, DMSO-d$_6$): δ=10.95 (s, 1H), 7.44 (s, 1H), 7.39 (d, J=7.3 Hz, 2H), 7.31 (t, J=7.3 Hz, 2H), 7.22-7.27 (m, 3H), 6.66 (d, J=8.6 Hz, 2H), 6.00 (t, J=6.3 Hz, 1H), 5.14 (s, 2H), 4.40 (t, J=6.3 Hz, 1H), 4.33 (t, J=6.3 Hz, 1H), 4.04 (t, J=6.3 Hz, 2H), 3.44 (q, J=6.6 Hz, 2H), 3.24-3.27 (m, 2H), 3.05 (q, J=6.3 Hz, 2H), 1.69 (quint, J=6.3 Hz, 2H), 1.50-1.62 (m, 4H), 1.24 (quint, J=6.3 Hz, 2H); IR (film): ν=3396, 3030, 2934, 2864, 1672, 1600, 1506, 1455, 1147, 1049, 700, 527 cm$^{-1}$; MS (LC/MS): m/z: calcd for C$_{28}$H$_{32}$N$_6$O$_4$H$^+$: 516.5, found: 517.2.

8-(2-Methoxyphenyl)-1-methyl-7-p-nitrophenyl-1H-imidazo[2,1-f]purine-2,4(3H,8H)-dione (27, LC-57)

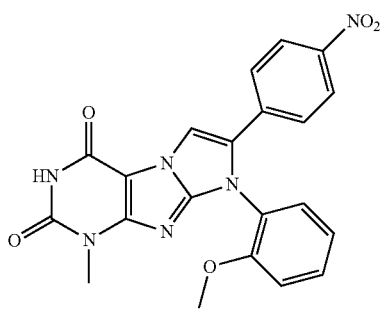

Yield: 63%; mp 323-325° C.; $^1$H NMR (400 MHz, DMSO-d$_6$): δ=11.06 (s, 1H), 8.35 (s, 1H), 8.14 (d, J=8.7 Hz, 2H), 7.64 (dd, J=7.6 Hz, J=1.1 Hz, 1H), 7.55 (dt, J=7.6 Hz, J=1.1 Hz, 1H), 7.51 (d, J=8.7 Hz, 2H), 7.21 (d, J=7.6 Hz, 1H), 7.16 (t, J=7.6 Hz, 1H), 3.54 (s, 3H), 3.30 (s, 3H); $^{13}$C NMR (100 MHz, DMSO-d$_6$): δ=154.4, 153.2, 153.1, 150.9, 148.4, 146.5, 134.8, 131.5, 130.7, 129.5, 127.6, 123.6, 122.1, 121.2, 113.1, 107.6, 99.1, 55.6, 28.8; IR (film): ν=3012, 2826, 1680, 1501, 1016, 844, 720, 600, 432 cm$^{-1}$; HRMS (ESI): m/z: calcd for C$_{21}$H$_{16}$N$_6$O$_5$Na$^+$: 455.1080, found: 455.1085.

8-(2-Methoxyphenyl)-1-methyl-7-p-cyanophenyl-1H-imidazo[2,1-f]purine-2,4(3H,8H)-dione (28, LC-60)

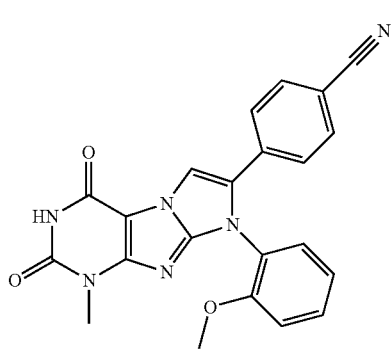

Yield: 68%; mp 303-305° C.; $^1$H NMR (400 MHz, DMSO-d$_6$): δ=11.04 (s, 1H), 8.28 (s, 1H), 7.77 (d, J=8.4 Hz, 2H), 7.62 (dd, J=7.6 Hz, J=1.2 Hz, 1H), 7.55 (dt, J=7.6 Hz, J=1.2 Hz, 1H), 7.43 (d, J=8.4 Hz, 2H), 7.20 (dd, J=7.6 Hz, J=1.2 Hz, 1H), 7.15 (dt, J=7.6 Hz, J=1.2 Hz, 1H), 3.53 (s, 3H), 3.30 (s, 3H); $^{13}$C NMR (100 MHz, DMSO-d$_6$): δ=154.4, 153.3, 153.0, 150.9, 148.3, 132.9, 132.3, 131.4, 131.1, 129.5, 127.3, 122.1, 121.2, 118.3, 113.0, 110.4, 107.1, 99.1, 55.6, 28.8; IR (film): ν=3010, 2835, 1680, 1497, 745, 605, 445 cm$^{-1}$; HRMS (ESI): m/z: calcd for C$_{22}$H$_{16}$N$_6$O$_3$Na$^+$: 435.1182, found: 435.1187.

8-(4-Hydroxybutyl)-7-p-(4-hydroxybutyl)-phenyl-1-methyl-1H-imidazo[2,1-f]purine-2,4(3H,8H)-dione (29, LC-66)

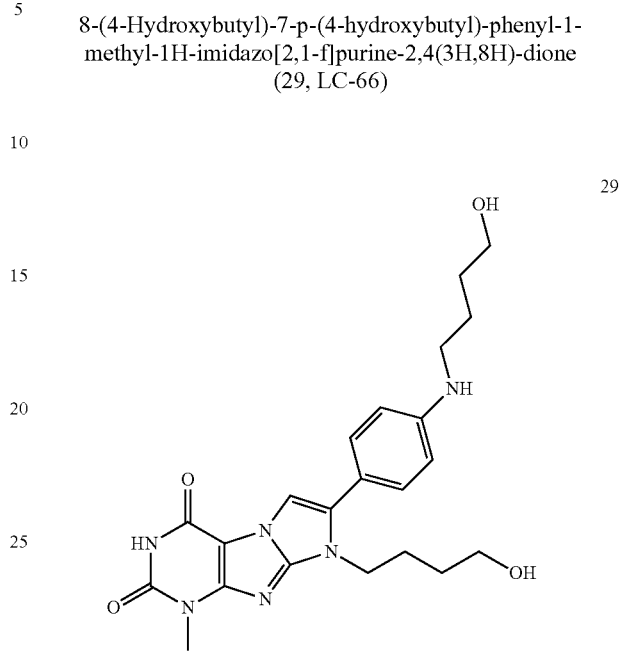

Yield: 29%; mp 205-207° C.; $^1$H NMR (400 MHz, DMSO-d$_6$): δ=7.43 (s, 1H), 7.23 (d, J=8.5 Hz, 2H), 6.65 (d, J=8.5 Hz, 2H), 6.00 (t, J=6.6 Hz, 1H), 4.41 (t, J=6.6 Hz, 1H), 4.36 (t, J=6.6 Hz, 1H), 4.04 (t, J=6.6 Hz, 2H), 3.44 (q, J=6.6 Hz, 2H), 3.39 (s, 3H), 3.28 (m, 2H), 3.05 (q, J=6.6 Hz, 2H), 1.69 (quint, J=6.6 Hz, 2H), 1.49-1.61 (m, 4H), 1.26 (quint, J=6.6 Hz, 2H), N$_3$H—not observed; $^{13}$C NMR (100 MHz, DMSO-d$_6$): δ=153.2, 152.4, 150.9, 149.5, 147.4, 133.3, 129.8, 113.9, 111.6, 103.3, 98.7, 60.4, 59.8, 43.3, 42.3, 30.0, 29.1, 28.7, 25.1, 25.1; IR (film): ν=3365, 3020, 2941, 2833, 1672, 1608, 1523, 1455, 1150, 1052, 615 cm$^{-1}$; HRMS (ESI): m/z: calcd for C$_{22}$H$_{28}$N$_6$O$_4$Na$^+$: 463.2070, found: 463.2070.

7-p-Fluorophenyl-8-(2-methoxyphenyl)-1H-imidazo[2,1-f]purine-2,4(3H,8H)-dione (30, LB-60)

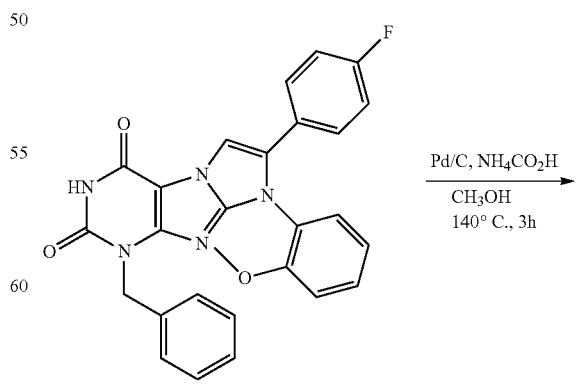

22

-continued

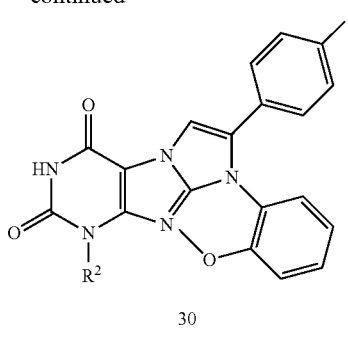

30

A mixture of LB-38 (22, 528 mg, 1.09 mmol), 10% Pd—C (339 mg) and dry ammonium formate (692 mg, 10.9 mmol) in absolute methanol (16 mL) was heated in a sealed tube at 140° C. for 3 h. The reaction was cooled to room temperature and the mixture was filtered over a short path of celite. The residue was evaporated under reduced pressure affording the desired compound as a white solid (121 mg, 28% yield). $^1$H NMR (400 MHz, DMSO-$d_6$): δ=11.53 (s, 1H), 10.71 (s, 1H), 7.96 (s, 1H), 7.47-7.51 (m, 2H), 7.28-7.31 (m, 2H), 7.13-7.18 (m, 3H), 7.06-7.10 (m, 1H), 3.56 (s, 3H); $^{13}$C NMR (100 MHz, DMSO-$d_6$): δ=162.4 (d, J=246.1 Hz), 155.1, 154.6, 152.7, 151.7, 148.8, 132.2, 131.7, 130.2 (d, J=8.4 Hz), 130.1, 125.3 (d, J=3.2 Hz), 122.8, 121.4, 115.9 (d, J=21.8 Hz), 113.3, 105.9, 99.5, 56.1; IR (film): ν=3159, 2900, 1668, 1500, 1393, 1242, 1065, 750, 536 cm$^{-1}$; MS (ESI): m/z: calcd for $C_{20}H_{14}FN_5O_3Na^+$: 414.3, found: 413.4.

General Procedure for the Alkylation at $N_1$

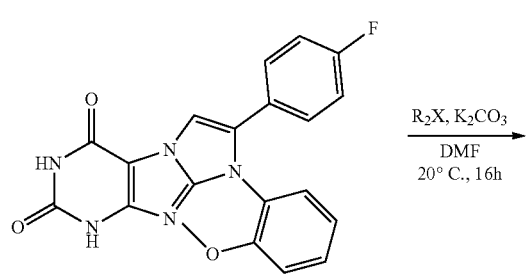

7-p-Fluorophenyl-8-(2-methoxyphenyl)-1H-imidazo[2,1-f]purine-2,4(3H,8H)-dione (30, 1.0 equiv) was dissolved in anhydrous DMF (concentration, 0.05 M), and potassium carbonate (1.0 equiv) was added. After stirring 5 min at room temperature, the corresponding alkylating agent (1.0 equiv) was added dropwise. The reaction was stirred at room temperature for 15 h. Potassium carbonate was then removed by filtration, and the mixture was evaporated under reduced pressure. The residue was purified by column chromatography on silica gel using a gradient $CH_2Cl_2$:EtOAc from 10:1 to 5:1. This method was used to obtain: LB-79 (31), LB-91 (32), LB-102 (33), LB-103 (34).

1,3-Bis-(2-ethoxy-2-oxoethyl)-7-(p-Fluorophenyl)-8-(2-methoxyphenyl)-1H-imidazo[2,1-f]purine-2,4(3H,8H)-dione (31, LB-79)

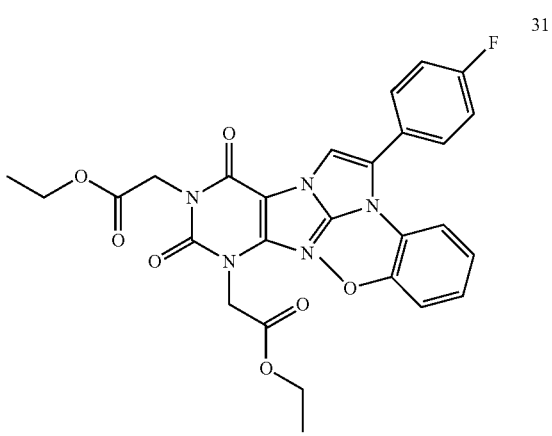 [SMILES: CCOC(=O)Cn1c(=O)c2c(nc3n(-c4ccccc4OC)c(-c4ccc(F)cc4)cn23)n(CC(=O)OCC)c1=O]

Yield: 17%; $^1$H NMR (400 MHz, CDCl$_3$): δ=7.56 (s, 1H), 7.43 (dt, J=7.6 Hz, J=1.4 Hz, 1H), 7.37 (dd, J=7.6 Hz, J=1.4 Hz, 1H), 7.13-7.16 (m, 2H), 7.06 (dt, J=7.6 Hz, J=1.4 Hz, 1H), 6.94-6.98 (m, 3H), 4.80 (s, 2H), 4.79 (s, 2H), 4.23 (q, J=7.1 Hz, 2H), 4.19 (q, J=7.1 Hz, 2H), 3.55 (s, 3H), 1.28 (t, J=7.1 Hz, 3H), 1.24 (t, J=7.1 Hz, 3H); $^{13}$C NMR (100 MHz, CDCl$_3$): δ=168.4, 167.7, 162.8 (d, J=249.3 Hz), 154.8, 153.2, 151.4, 151.3, 148.1, 132.6, 131.0, 129.7 (d, J=8.3 Hz), 129.3, 124.7 (d, J=3.5 Hz), 122.6, 121.1, 115.7 (d, J=21.9 Hz), 112.5, 105.4, 99.7, 61.5, 61.4, 55.4, 44.3, 42.0, 14.1, 14.0; IR (film): ν=3015, 2952, 1746, 1715, 1665, 1495, 1210, 751, 536 cm$^{-1}$; MS (ESI): m/z: calcd for $C_{28}H_{26}FN_5O_7Na^+$: 586.5, found: 586.2.

8-(2-Methoxyphenyl)-1-(methoxy-2-oxoethyl)-7-(p-Fluorophenyl)-1H-imidazo[2,1-f]purine-2,4(3H,8H)-dione (32, LB-91)

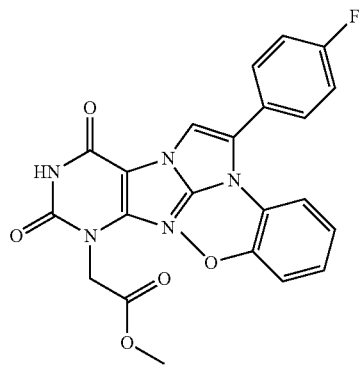

Yield: 23%; $^1$H NMR (500 MHz, CDCl$_3$): δ=8.03 (s, 1H), 7.58 (s, 1H), 7.43 (dt, J=7.7 Hz, J=1.5 Hz, 1H), 7.37 (dd, J=7.7 Hz, J=1.5 Hz, 1H), 7.14-7.17 (m, 2H), 7.06 (t, J=7.7 Hz, 1H), 6.95-6.99 (m, 3H), 4.78 (s, 2H), 3.74 (s, 3H), 3.55 (s, 3H); MS (LC/MS): m/z: calcd for $C_{23}H_{18}FN_5O_5H^+$: 464.4, found: 464.2.

8-(2-Methoxyphenyl)-1,3-bis-(methoxy-2-oxoethyl)-7-(p-Fluorophenyl)-1H-imidazo[2,1-f]purine-2,4(3H,8H)-dione (33, LB-102)

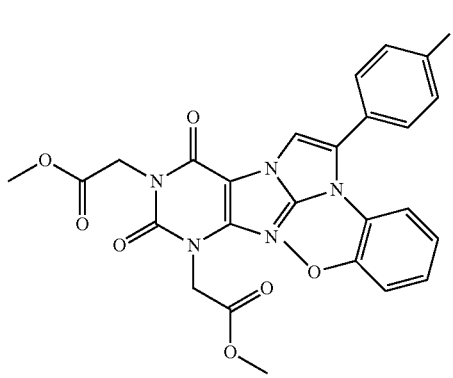

Yield: 27%; $^1$H NMR (400 MHz, CDCl$_3$): δ=7.57 (s, 1H), 7.44 (dt, J=7.7 Hz, J=1.4 Hz, 1H), 7.37 (dd, J=7.7 Hz, J=1.4 Hz, 1H), 7.13-7.17 (m, 2H), 7.06 (dt, J=7.7 Hz, J=1.4 Hz, 1H), 6.94-6.98 (m, 3H), 4.83 (s, 2H), 4.82 (s, 2H), 3.77 (s, 3H), 3.74 (s, 3H), 3.56 (s, 3H); MS (ESI): m/z: calcd for C$_{26}$H$_{22}$FN$_5$O$_7$Na$^+$: 558.4, found: 558.2.

8-(2-Methoxyphenyl)-1-(methylthiomethyl)-7-(p-Fluorophenyl)-1H-imidazo[2,1-f]purine-2,4(3H,8H)-dione (34, LB-103)

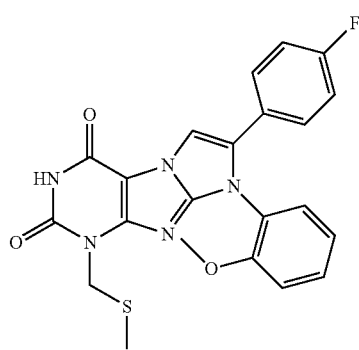

Yield: 18%; $^1$H NMR (500 MHz, CDCl$_3$): δ=7.92 (s, 1H), 7.58 (s, 1H), 7.44 (t, J=7.7 Hz, 1H), 7.34 (d, J=7.7 Hz, 1H), 7.14-7.17 (m, 2H), 7.06 (t, J=7.7 Hz, 1H), 6.95-6.99 (m, 3H), 5.16 (d, 2H), 3.59 (s, 3H), 2.32 (s, 3H); $^{13}$C NMR (100 MHz, CDCl$_3$): δ=162.8 (d, J=249.7 Hz), 154.7, 152.9, 152.6, 150.6, 148.3, 132.7, 131.0, 129.7 (d, J=8.3 Hz), 129.2, 124.6 (d, J=3.2 Hz), 122.5, 121.2, 115.7 (d, J=21.8 Hz), 112.6, 105.4, 100.0, 55.5, 46.4, 16.1; IR (film): ν=3166, 3045, 2963, 2817, 1672, 1504, 1259, 1159, 1021, 740, 584 cm$^{-1}$; MS (LC/MS): m/z: calcd for C$_{22}$H$_{18}$FN$_5$O$_3$SH$^+$: 452.4, found: 452.2.

8-(2-Methoxyphenyl)-1-(methylsulfonylmethyl)-7-(p-Fluorophenyl)-1H-imidazo[2,1-f]purine-2,4(3H,8H)-dione (35, LB-104)

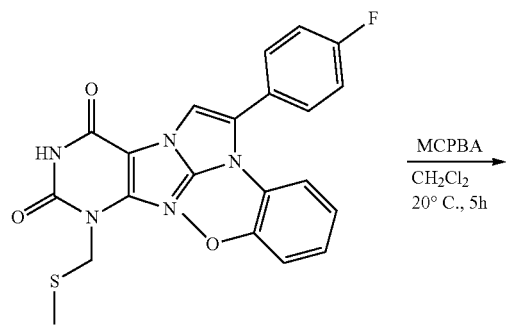

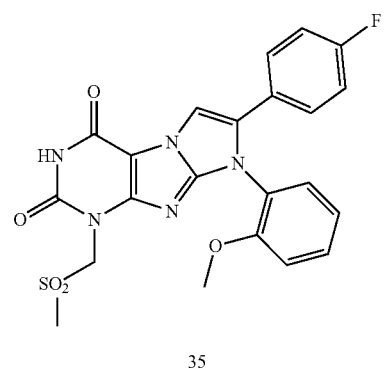

A solution of LB-103 (34, 6.9 mg, 0.015 mmol) in dry CH$_2$Cl$_2$ (1 mL) was treated with m-CPBA (6.59 mg, 0.038 mmol). The reaction mixture was stirred at room temperature for 5 h, till no starting material was visible by TLC. The reaction mixture was quenched by washing with saturated aq. NaHCO$_3$ (2×10 mL) and the aqueous layer was then extracted with CH$_2$Cl$_2$. The organic extracts were dried over MgSO$_4$ and evaporated under reduced pressure. Purification by column chromatography on silica gel using a gradient CH$_2$Cl$_2$:EtOAc from 10:1 to 5:1 afforded the desired compound as a white solid (0.3 mg, 4% yield). $^1$H NMR (400 MHz, CDCl$_3$): δ=7.86 (s, 1H), 7.58 (s, 1H), 7.45 (dt, J=7.6 Hz, J=1.4 Hz, 1H), 7.30 (dd, J=7.6 Hz, J=1.4 Hz, 1H), 7.14-7.17 (m, 2H), 7.05 (dt, J=7.6 Hz, J=1.4 Hz, 1H), 6.95-7.00 (m, 3H), 5.34 (s, 2H), 3.60 (s, 3H), 3.10 (s, 3H); MS (LC/MS): m/z: calcd for C$_{22}$H$_{18}$FN$_5$O$_5$SH$^+$: 483.4, found: 484.1.

General Procedure for the Bromination

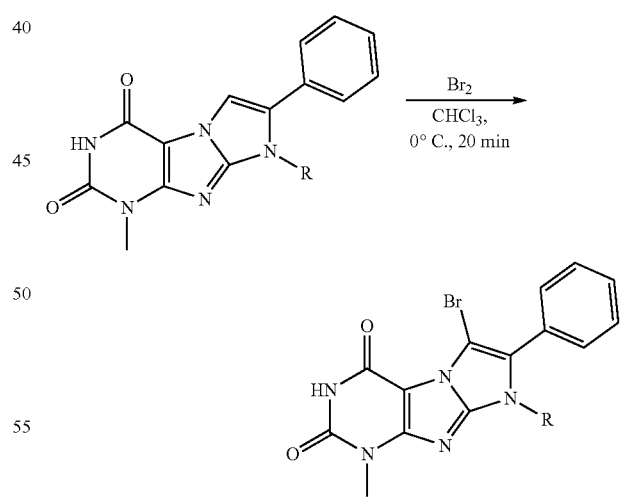

To a solution of the corresponding imidazoxanthine (1.0 equiv) in chloroform (concentration, 0.2 M) at 0° C. was added bromine (1.0 equiv) dropwise over 1 h and stirring was continued for 2 h. The solid was filtered off, washed with water affording the corresponding products in pure form. This method was used to obtain: LB-32 (36), LB-22 (37), LB-23 (38).

1-Benzyl-6-bromo-7-p-fluorophenyl-8-phenyl-1H-imidazo[2,1-f]purine-2,4(3H,8H)-dione (36, LB-32)

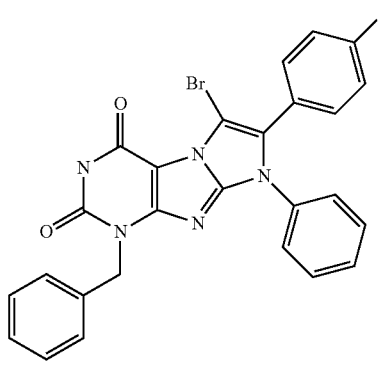

Yield: 33%; mp 276-278° C.; $^1$H NMR (400 MHz, DMSO-$d_6$): δ=11.11 (s, 1H), 7.23-7.46 (m, 14H), 5.09 (s, 2H); $^{13}$C NMR (100 MHz, DMSO-$d_6$): δ=162.3 (d, J=247.6 Hz), 152.7, 152.4, 150.4, 146.9, 136.8, 133.7, 132.9 (d, J=8.8 Hz), 129.3, 129.0, 128.5, 128.2, 127.1 (2C), 126.7, 123.2 (d, J=3.2 Hz), 115.6 (d, J=21.8 Hz), 100.0, 91.7, 44.9; IR (film): ξ=3164, 3032, 2838, 1674, 1480, 1254, 1157, 747, 691 cm$^{-1}$; MS (ESI): m/z: calcd for $C_{26}H_{17}BrFN_5O_2Na^+$: 553.4, found: 554.0.

6-Bromo-8-(2-methoxyphenyl)-1-methyl-7-phenyl-1H-imidazo[2,1-f]purine-2,4(3H,8H)-dione (37, LB-22)

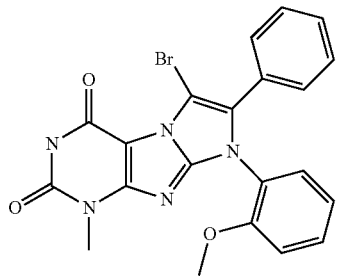

Quantitative yield; mp 274-276° C.; $^1$H NMR (400 MHz, DMSO-$d_6$): δ=10.97 (s, 1H), 7.54 (dd, J=7.8 Hz, J=1.2 Hz, 1H), 7.43 (dt, J=7.8 Hz, J=1.2 Hz, 1H), 7.34-7.36 (m, 3H), 7.28-7.30 (m, 2H), 7.10 (d, J=7.8 Hz, 1H), 7.04 (dt, J=7.8 Hz, J=1.2 Hz, 1H), 3.56 (s, 3H), 3.29 (s, 3H); $^{13}$C NMR (100 MHz, DMSO-$d_6$): δ=154.6, 153.1, 152.4, 150.7, 147.3, 131.4, 131.0, 129.8, 129.7, 129.1, 128.2, 126.8, 122.0, 120.8, 112.7, 100.0, 90.4, 55.6, 28.8; IR (film): ν=3155, 3029, 2832, 1676, 1495, 1159, 746 cm$^{-1}$; HRMS (ESI): m/z: calcd for $C_{21}H_{16}BrN_5O_3Na^+$: 488.0334, found: 488.0338.

6-Bromo-8-butyl-1-methyl-7-phenyl-1H-imidazo[2,1-f]purine-2,4(3H,8H)-dione (38, LB-23)

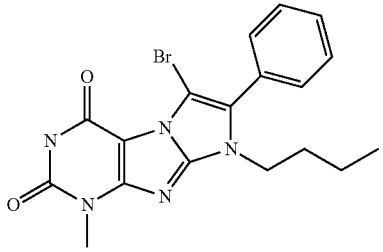

Quantitative yield; mp 302-304° C.; $^1$H NMR (400 MHz, DMSO-$d_6$): δ=10.89 (s, 1H), 7.54-7.60 (m, 5H), 3.98 (t, J=7.3 Hz, 2H), 3.39 (s, 3H), 1.54 (quint, J=7.3 Hz, 2H), 1.08 (sext, J=7.3 Hz, 2H), 0.69 (t, J=7.3 Hz, 3H); $^{13}$C NMR (100 MHz, DMSO-$d_6$): δ=153.0, 152.3, 150.7, 147.2, 130.3, 129.9, 129.6, 128.8, 126.6, 99.7, 89.5, 43.9, 29.9, 28.7, 18.6, 12.9; IR (film): ν=3167, 2958, 2820, 1698, 1669, 1504, 1444, 1154, 743, 581 cm$^{-1}$; MS (ESI): m/z: calcd for $C_{18}H_{18}BrN_5O_2Na^+$: 439.2, found: 438.1.

6-Hydroxymethyl-8-(2-methoxyphenyl)-1-methyl-7-phenyl-1H-imidazo[2,1-f]purine-2,4(3H,8H)-dione (39, LB-30)

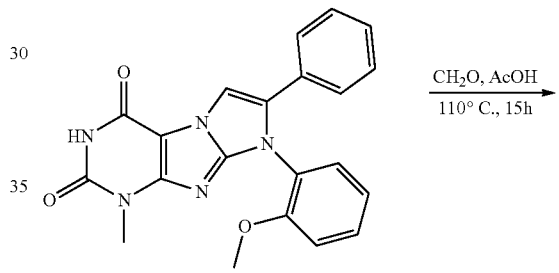

A mixture of commercially available 8-(2-methoxyphenyl)-1-methyl-7-phenyl-1H-imidazo[2,1-f]purine-2,4(3H, 8H)-dione (5, 100 mg, 0.258 mmol) in acetic acid (0.387 mL) and formalin (36%, 1.1 mL) was refluxed for 15 h. The solution was then was cooled to room temperature and neutralized with sat. $Na_2CO_3$, and the resulting precipitate was filtered off. Cristallization in methanol afforded the desired product as a white solid (6 mg, 5% yield). $^1$H NMR (500 MHz, DMSO-$d_6$): δ=11.27 (s, 1H), 7.49 (d, J=7.8 Hz, 1H), 7.45 (t, J=7.8 Hz, 1H), 7.32-7.37 (m, 3H), 7.23-7.24 (m, 2H), 7.12 (d, J=7.8 Hz, 1H), 7.05 (t, J=7.8 Hz, 1H), 5.90-5.93 (m, 1H), 4.69-4.72 (m, 2H), 3.55 (s, 3H), 3.32 (s, 3H); $^{13}$C NMR (125 MHz, DMSO-$d_6$): δ=154.7, 154.5, 153.6, 150.6, 147.1, 131.1, 129.7, 129.4, 129.2, 128.7, 128.2, 127.0, 122.1, 120.7, 119.4, 112.7, 99.4, 55.5, 52.9, 28.9; IR (film): ν=3134, 2995, 2806, 1668, 1496, 1024, 749, 596 cm$^{-1}$; HRMS (ESI): m/z: calcd for $C_{22}H_{19}N_5O_4Na^+$: 440, 1335, found: 440, 1336.

6-Acetyl-8-(2-methoxyphenyl)-1-methyl-7-phenyl-1H-imidazo[2,1-f]purine-2,4(3H,8H)-dione (40, LC-54)

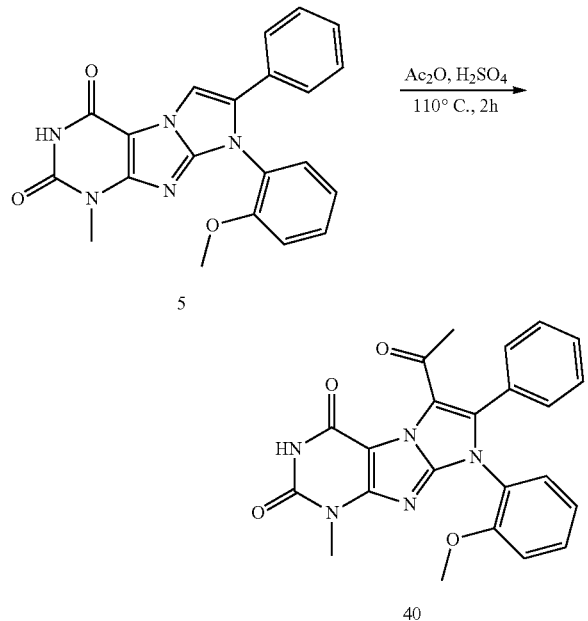

A mixture of commercially available 8-(2-methoxyphenyl)-1-methyl-7-phenyl-1H-imidazo[2,1-f]purine-2,4(3H,8H)-dione (5, 200 mg, 0.516 mmol) in concentrated $H_2SO_4$ (0.103 mL) and acetic anhydride (1.29 mL) was refluxed for 2 h. The reaction was cooled to room temperature, poured into 10 mL of water, and extracted with $CH_2Cl_2$ (2×10 mL). The organic extracts were dried over $MgSO_4$ and evaporated under reduced pressure. Purification by column chromatography on silica gel using a gradient $CH_2Cl_2$:EtOAc from 5:1 to 1:1 afforded the desired compound as a white solid (88 mg, 39% yield). $^1$H NMR (500 MHz, DMSO-$d_6$): δ=11.03 (s, 1H), 7.54 (d, J=7.9 Hz, 1H), 7.42 (t, J=7.8 Hz, 1H), 7.30-7.37 (m, 5H), 7.08 (d, J=7.9 Hz, 1H), 7.02 (t, J=7.8 Hz, 1H), 3.60 (s, 3H), 3.30 (s, 3H), 2.46 (s, 3H); $^{13}$C NMR (100 MHz, DMSO-$d_6$, CDCl$_3$): δ=187.6, 154.4, 153.6, 153.0, 150.6, 146.8, 135.7, 131.4, 130.7, 129.8, 129.6, 127.5, 126.4, 121.2, 120.6, 120.1, 112.5, 101.0, 55.5, 29.6, 28.8; IR (film): ν=3160, 3050, 1668, 1490, 1292, 1211, 1023, 751, 555 cm$^{-1}$; HRMS (ESI): m/z: calcd for $C_{23}H_{19}N_5O_4Na^+$: 452.1335, found: 452.1338.

6-Cyano-8-(2-methoxyphenyl)-1-methyl-7-phenyl-1H-imidazo[2,1-f]purine-2,4(3H,8H)-dione (41, LC-55)

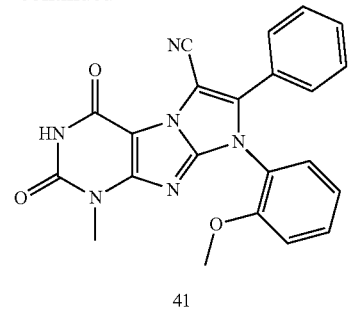

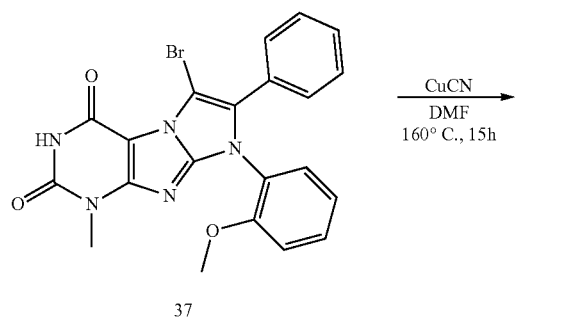

To a solution of LB-22 (37, 140 mg, 0.3 mmol) in DMF (2 mL) was added CuCN (80 mg, 0.9 mmol). The resulting mixture was heated to 160° C. overnight. The reaction was then cooled, poured into 10 mL of 10% aq. NaCN, and the resulting precipitate was filtered off, affording the desired product as a white solid in pure form. (51 mg, 41% yield). $^1$H NMR (400 MHz, DMSO-$d_6$): δ=11.22 (s, 1H), 7.62 (dd, J=8 Hz, J=1.3 Hz, 1H), 7.52 (dt, J=8 Hz, J=1.3 Hz, 1H), 7.37-7.48 (m, 5H), 7.16 (dd, J=8 Hz, J=1.3 Hz, 1H), 7.11 (dt, J=8 Hz, J=1.3 Hz, 1H), 3.56 (s, 3H), 3.30 (s, 3H); $^{13}$C NMR (125 MHz, DMSO-$d_6$): δ=154.3, 153.0, 152.6, 150.7, 146.5, 142.9, 131.9, 130.6, 129.6, 128.7, 128.7, 124.9, 121.0, 120.9, 112.9, 110.6, 100.9, 91.8, 55.7, 28.8; IR (film): ν=3151, 3028, 2811, 1675, 1495, 1159, 1282, 1014, 740, 551 cm$^{-1}$; HRMS (ESI): m/z: calcd for $C_{22}H_{16}N_6O_3Na^+$: 435.1182, found: 435.1181.

8-(Butylamino)-3,7-dihydro-3-methyl-7-(2-oxo-2-phenylethyl)-1H-Purine-2,6-dione (43, LC-59)

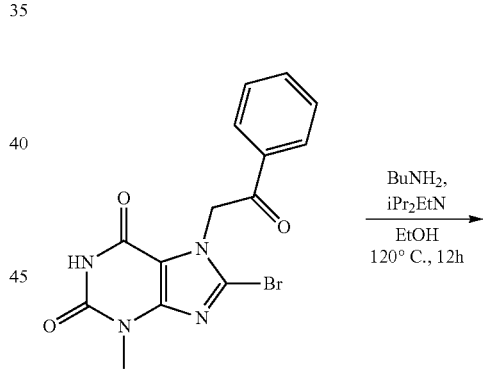

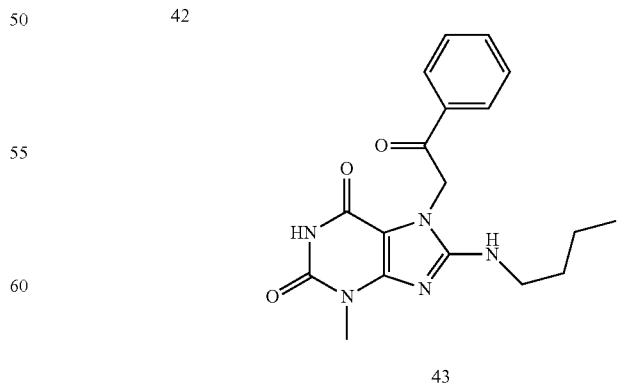

A mixture of commercially available 8-bromo-3,7-dihydro-3-methyl-7-(2-oxo-2-phenylethyl)-1H-purine-2,6-dione (42, 50 mg, 0.138 mmol), diisopropylethylamine (47 μL, 0.275 mmol) and butylamine (27 μL, 0.275 mmol) in EtOH (1 mL) was heated at 120° C. for 12 h. The reaction was cooled to room temperature, the solid was filtered off, washed with water, affording the desired product as a white solid (22 mg, 44% yield). $^1$H NMR (400 MHz, DMSO-$d_6$): δ=11.57 (s, 1H), 8.04 (d, J=7.8 Hz, 2H), 7.72 (t, J=7.8 Hz, 1H), 7.60 (t, J=7.8 Hz, 2H), 6.99 (t, J=5.5 Hz, 1H), 5.62 (s, 2H), 3.32 (s, 3H), 3.32 (m, 2H), 1.51 (quint, J=7.4 Hz, 2H), 1.31 (sext, J=7.4 Hz, 2H), 0.88 (t, J=7.4 Hz, 3H); $^{13}$C NMR (125 MHz, DMSO-$d_6$): δ=192.2, 154.6, 153.0, 150.7, 150.0, 134.1, 133.8, 128.7, 127.9, 101.7, 49.5, 41.8, 31.0, 28.2, 19.2, 13.5; IR (film): ν=3361, 3008, 2827, 1681, 1485, 1425, 1230, 746 cm$^{-1}$; HRMS (ESI): m/z: calcd for $C_{18}H_{21}N_5O_3Na^+$: 378.1542, found: 378.1545.

8-(2-Methoxyphenyl)-1-methyl-7-p-carboxyphenyl-1H-imidazo[2,1-f]purine-2,4(3H,8H)-dione (44, LC-69)

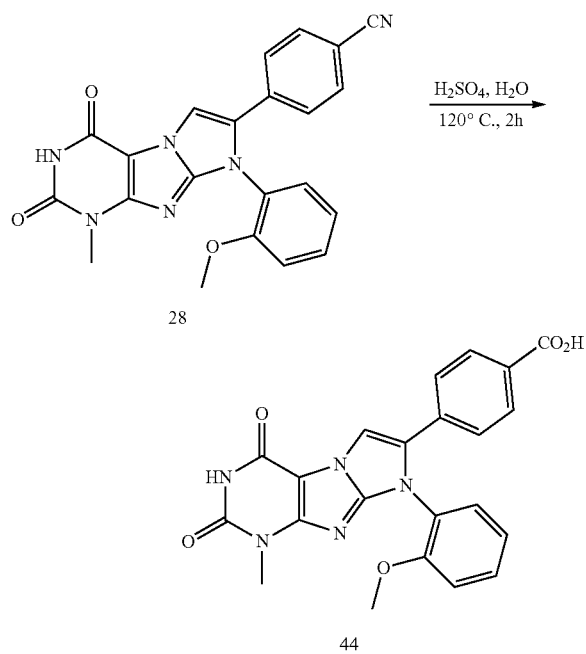

8-(2-Methoxyphenyl)-1-methyl-7-p-cyanophenyl-1H-imidazo[2,1-f]purine-2,4(3H,8H)-dione (28, LC-55, 85 mg, 0.206 mmol) was dissolved in water (0.910 mL) and conc. H$_2$SO$_4$ (0.803 mL) and refluxed for 2 h. The reaction mixture was then cooled to room temperature, 1 mL of water was added, and the precipitate was filtered off, affording the desired product as a white solid (60 mg, 67% yield). $^1$H NMR (400 MHz, DMSO-$d_6$): δ=11.02 (s, 1H), 8.16 (s, 1H), 7.82 (d, J=8.3 Hz, 2H), 7.58 (dd, J=7.7 Hz, J=1.4 Hz, 1H), 7.53 (dt, J=7.7 Hz, J=1.4 Hz, 1H), 7.37 (d, J=8.3 Hz, 2H), 7.19 (d, J=7.6 Hz, 1H), 7.14 (t, J=7.6 Hz, 1H), 3.54 (s, 3H), 3.30 (s, 3H), CO$_2$H—not observed; $^{13}$C NMR (100 MHz, DMSO-$d_6$): δ=166.6, 154.6, 153.3, 152.9, 150.9, 148.2, 132.3, 131.9, 131.3, 130.2, 129.5, 129.2, 127.0, 122.3, 121.1, 113.0, 106.4, 99.1, 55.6, 28.8; IR (film): ν=3013, 2839, 1681, 1547, 1264, 1158, 1013, 745, 570 cm$^{-1}$; HRMS (ESI): m/z: calcd for $C_{22}H_{17}N_5O_5Na^+$: 454.1127, found: 454.1135.

8-Butyl-1-methyl-6-nitro-7-phenyl-1H-imidazo[2,1-f]purine-2,4(3H,8H)-dione (45, LC-80)

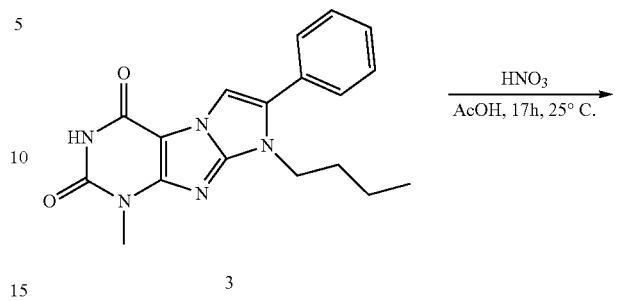

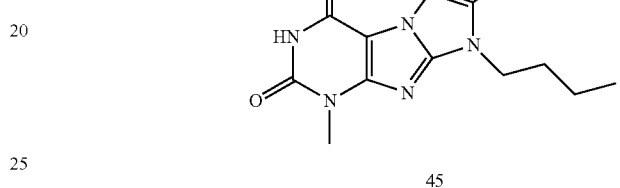

To a solution of commercially available 8-butyl-1-methyl-7-phenyl-1H-imidazo[2,1-f]purine-2,4(3H,8H)-dione (3, 100 mg, 0.296 mmol) in acetic acid (500 μL) was added HNO$_3$ (fuming, 24 μL, 0.592 mmol), and the resulting mixture was stirred at room temperature for 12 h. Water was added, and the resulting precipitate was filtered off. Cristallization in methanol afforded the desired product as a yellow solid (26 mg, 23% yield). $^1$H NMR (400 MHz, DMSO-$d_6$): δ=11.05 (s, 1H), 7.60-7.69 (m, 5H), 3.93 (t, J=7.3 Hz, 2H), 3.43 (s, 3H), 1.62 (quint, J=7.3 Hz, 2H), 1.14 (sext, J=7.3 Hz, 2H), 0.70 (t, J=7.3 Hz, 3H); $^{13}$C NMR (100 MHz, DMSO-$d_6$): δ=153.4, 152.1, 150.5, 144.6, 134.4, 130.9, 130.7, 128.5, 126.9, 124.7, 101.6, 44.3, 29.5, 29.0, 18.6, 12.9; IR (film) ν=3172, 3052, 2964, 1693, 1502, 1356, 1294, 732, 577 cm$^{-1}$; HRMS (ESI): m/z: calcd for $C_{18}H_{18}N_6O_4Na^+$: 405.1287, found: 405.1288.

The invention claimed is:

1. A compound of formula 1

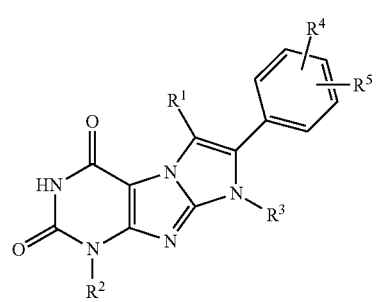

wherein

R$^1$ is hydrogen,

R$^2$ is lower alkyl, arylsulfonyl, heteroarylsulfonyl, lower alkylsulfonyl, aminosulfonyl, lower alkylaminosulfonyl, arylcarbonyl, heteroarylcarbonyl, lower alkylcarbonyl, lower alkoxycarbonyl, aminocarbonyl, lower alkylaminocarbonyl or carboxy;

$R^3$ is alkyl, hydroxy-lower alkyl, methoxy-lower alkyl, aryl-lower alkyl, or heteroaryl-lower alkyl;

$R^4$ is para-fluoro or para-chloro; and $R^5$ is hydrogen;

or wherein $R^1$ is hydrogen, $R^2$ is lower alkyl, arylsulfonyl, heteroarylsulfonyl, lower alkylsulfonyl, aminosulfonyl, lower alkylaminosulfonyl, arylcarbonyl, heteroarylcarbonyl, lower alkylcarbonyl, lower alkoxycarbonyl, aminocarbonyl, lower alkylaminocarbonyl or carboxy;

$R^3$ is alkyl, hydroxy-lower alkyl, methoxy-lower alkyl, aryl-lower alkyl, heteroaryl-lower alkyl or aryl; and $R^4$ and $R^5$ are, independently of each other, hydrogen, ortho- or meta-fluoro, ortho- or meta-chloro, ortho- or meta-methoxy, ortho-nitro, ortho-, meta- or para-methyl, or ortho-, meta- or para-hydroxy; and wherein at least one of $R^4$ and $R^5$ is different from hydrogen;

and tautomers and salts thereof.

2. The compound of formula 1 according to claim 1, wherein $R^3$ is lower alkyl, hydroxy-lower alkyl, methoxy-lower alkyl, optionally substituted phenyl-lower alkyl, pyridyl-, pyrrolyl-, pyrazolyl- or imidazolyl-lower alkyl, or optionally substituted phenyl;

and $R^1$, $R^2$, $R^4$ and $R^5$ have the indicated meanings;

and tautomers and salts thereof.

3. The compound of formula 1 according to claim 1, wherein $R^3$ is lower alkyl, hydroxy-lower alkyl, methoxy-lower alkyl, phenyl-lower alkyl, pyridyl-lower alkyl, or phenyl optionally substituted by one or two substituents lower alkyl, lower alkoxy, halo-lower alkyl or halo;

and $R^1$, $R^2$, $R^4$ and $R^5$ have the indicated meanings;

and tautomers and salts thereof.

4. The compound of formula 1 according to claim 1, wherein $R^3$ is lower alkyl, hydroxy-lower alkyl, methoxy-lower alkyl, or phenyl optionally substituted by one or two substituents lower alkyl or lower alkoxy;

and $R^1$, $R^2$, $R^4$ and $R^5$ have the indicated meanings;

and tautomers and salts thereof.

5. The compound of formula 1

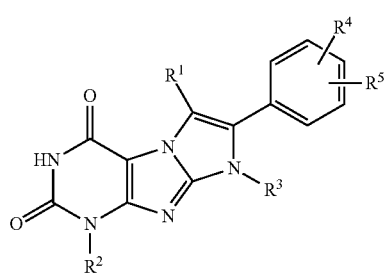

wherein $R^1$ is hydrogen, $R^2$ is lower alkyl, arylsulfonyl, heteroarylsulfonyl, lower alkylsulfonyl, aminosulfonyl, lower alkylaminosulfonyl, arylcarbonyl, heteroarylcarbonyl, lower alkylcarbonyl, lower alkoxycarbonyl, aminocarbonyl, lower alkylaminocarbonyl or carboxy;

$R^3$ is alkyl, hydroxy-lower alkyl, methoxy-lower alkyl, aryl-lower alkyl, or heteroaryl-lower alkyl;

$R^4$ is para-fluoro or para-chloro; and $R^5$ is hydrogen;

and tautomers and salts thereof.

6. The compound of formula 1 according to claim 1, wherein $R^1$ is hydrogen, $R^2$ is lower alkyl, arylsulfonyl, heteroarylsulfonyl, lower alkylsulfonyl, aminosulfonyl, lower alkylaminosulfonyl, arylcarbonyl, heteroarylcarbonyl, lower alkylcarbonyl, lower alkoxycarbonyl, aminocarbonyl, lower alkylaminocarbonyl or carboxy;

$R^3$ is alkyl, hydroxy-lower alkyl, methoxy-lower alkyl, aryl-lower alkyl, heteroaryl-lower alkyl or aryl; and $R^4$ and $R^5$ are, independently of each other, hydrogen, ortho- or meta-fluoro, ortho- or meta-chloro, ortho- or meta-methoxy, ortho-nitro, ortho-, meta- or para-methyl, or ortho, meta- or para-hydroxy; and wherein at least one of $R^4$ and $R^5$ is different from hydrogen;

and tautomers and salts thereof.

7. A pharmaceutical preparation comprising a compound of formula 1

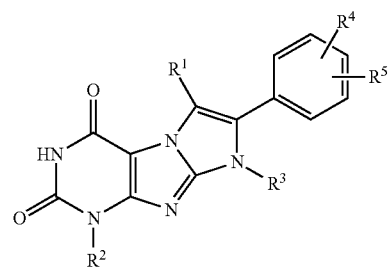

wherein $R^1$ is hydrogen, $R^2$ is lower alkyl, arylsulfonyl, heteroarylsulfonyl, lower alkylsulfonyl, aminosulfonyl, lower alkylaminosulfonyl, arylcarbonyl, heteroarylcarbonyl, lower alkylcarbonyl, lower alkoxycarbonyl, aminocarbonyl, lower alkylaminocarbonyl or carboxy;

$R^3$ is alkyl, hydroxy-lower alkyl, methoxy-lower alkyl, aryl-lower alkyl, or heteroaryl-lower alkyl;

$R^4$ is para-fluoro or para-chloro; and $R^5$ is hydrogen;

and tautomers and salts thereof.

8. A pharmaceutical preparation according to claim 7 comprising a compound of formula 1, wherein $R^1$ is hydrogen, $R^2$ is lower alkyl, arylsulfonyl, heteroarylsulfonyl, lower alkylsulfonyl, aminosulfonyl, lower alkylaminosulfonyl, arylcarbonyl, heteroarylcarbonyl, lower alkylcarbonyl, lower alkoxycarbonyl, aminocarbonyl, lower alkylaminocarbonyl or carboxy;

$R^3$ is alkyl, hydroxy-lower alkyl, methoxy-lower alkyl, aryl-lower alkyl, heteroaryl-lower alkyl or aryl; and $R^4$ and $R^5$ are, independently of each other, hydrogen, ortho- or meta-fluoro, ortho- or meta-chloro, ortho- or meta-methoxy, ortho-nitro, ortho-, meta- or para-methyl, or ortho-, meta- or para-hydroxy; and wherein at least one of $R^4$ and $R^5$ is different from hydrogen; and tautomers and salts thereof.

* * * * *